US006566338B1

(12) United States Patent
Weber et al.

(10) Patent No.: US 6,566,338 B1
(45) Date of Patent: May 20, 2003

(54) CASPASE INHIBITORS FOR THE TREATMENT AND PREVENTION OF CHEMOTHERAPY AND RADIATION THERAPY INDUCED CELL DEATH

(75) Inventors: Eckard Weber, San Diego, CA (US); Gordon B. Mills, Houston, TX (US); Douglas R. Green, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 09/685,689

(22) Filed: Oct. 11, 2000

Related U.S. Application Data

(60) Provisional application No. 60/187,868, filed on Mar. 8, 2000, and provisional application No. 60/158,385, filed on Oct. 12, 1999.

(51) Int. Cl.[7] .............................. A61K 38/05; C07K 4/00
(52) U.S. Cl. ............................... 514/19; 514/18; 514/2; 436/86; 436/90; 435/219; 435/366; 435/404; 260/998.2
(58) Field of Search ............................... 514/19, 18, 2; 436/86, 90; 435/219, 404, 366; 260/998.2

(56) References Cited

U.S. PATENT DOCUMENTS

| | | | |
|---|---|---|---|
| 4,153,688 A | 5/1979 | Domicoli et al. | ............ 424/177 |
| 4,518,528 A | 5/1985 | Rasnick | ............ 260/112.5 |
| 5,416,013 A | 5/1995 | Black et al. | ............ 435/226 |
| 5,430,128 A | 7/1995 | Chapman et al. | ............ 530/330 |
| 5,434,248 A | 7/1995 | Chapman et al. | ............ 530/330 |
| 5,462,939 A | 10/1995 | Dolle et al. | ............ 514/231.5 |
| 5,585,357 A | 12/1996 | Dolle et al. | ............ 514/18 |
| 5,624,672 A | 4/1997 | Bathurst et al. | ......... 424/195.1 |
| 5,635,186 A | 6/1997 | Bathurst et al. | ......... 424/195.1 |
| 5,635,187 A | 6/1997 | Bathurst et al. | ......... 424/195.1 |
| 5,677,283 A | 10/1997 | Dolle et al. | ............ 514/18 |
| 5,756,465 A | 5/1998 | Sleath et al. | ............ 514/17 |
| 5,843,904 A | 12/1998 | Bemis et al. | ............ 514/18 |
| 5,866,545 A | 2/1999 | Hagmann et al. | ............ 514/18 |
| 5,869,519 A | 2/1999 | Karanewsky et al. | ....... 514/415 |
| 5,871,724 A * | 2/1999 | Itawa et al. | ............ 424/85.1 |
| 5,932,549 A | 8/1999 | Allen et al. | ............ 514/18 |
| 6,136,787 A | 10/2000 | Black et al. | ............ 514/18 |
| 6,153,591 A | 11/2000 | Cai et al. | ............ 514/19 |
| 6,184,210 B1 | 2/2001 | Keana et al. | ............ 514/19 |
| 6,200,969 B1 | 3/2001 | Fritz et al. | ............ 514/214 |

FOREIGN PATENT DOCUMENTS

| | | |
|---|---|---|
| EP | 0 519 748 A2 | 12/1992 |
| EP | 0 618 223 A2 | 10/1994 |
| JP | 11-180891 | 7/1999 |
| WO | WO 93/05071 | 3/1993 |
| WO | WO 96/03982 | 2/1996 |
| WO | WO 96/20721 | 7/1996 |
| WO | WO 98/10778 | 3/1998 |
| WO | WO 98/111090 | 3/1998 |
| WO | WO 98/41232 | 9/1998 |
| WO | WO 99/18781 | 4/1999 |
| WO | WO 9918781 * | 4/1999 |
| WO | WO 99/47154 | 9/1999 |
| WO | WO 9947154 * | 9/1999 |
| WO | WO 00/55114 | 9/2000 |
| WO | WO 00/61542 | 10/2000 |

OTHER PUBLICATIONS

Alnermi, E.S. et al., "Human ICE/CED–3 Protease Nomenclature," *Cell* 87:171, Cell Press, Cambridge, MA (1996).

An, S. and Knox, K.A., "Ligation of CD40 rescues Ramos–Burkitt lymphoma B cells from calcium ionophore– and antigen receptor–triggered by inhibiting activation of the cysteine proteas CPP32/Yana and cleavage of aopoptosis its substrate PARP," *FEBS Lett*. 386:115–122, Elsevier Science Publishers B.V., Amsterdam (1996).

Angliker, H. et al., "The synthesis of lysylfluoromethanes and their properties an inhibitors of trypsim plasmin and cathepsin B," *Biochem J*. 241:871–875, The Biochemical Society, London England (1987).

Black, R.A. et al., A Pre–aspartate–specific Protease from Human Leukocytes That Cleaves Pro–interleukin 1α, *J. Biol. Chem*. 264.5323–5326, The American Society for Biochemistry and Molecular Biology, Baltimore, MD (1989).

Black, S.C. et al., "Co–localization of the Cysteine Protease Caspase–3 with Apoptotic Myocytes after In Vivo Myocardial Ischemia and Reperfusion in the Rat, " *J. Mol. Cell. Cardiol*. 30.733–742, Academic Press, Inc., New York, NY (Apr. 1998).

Bourne, E.J. et al., "Studies of Trifluoroacetic Acid. Part XVIII. Reaction of N–Aroylglycines with Perfluoro–carboxylic Anhydrides." *J. Chem. Soc*. Part, II:1771–1775, The Chemical Society, London, England (1961).

Conaldi, P.G. et al., "HIV–1 Kills Renal Tubular Epithelial Cells in Vitro by Triggering an Apoptotic Pathway Involving Caspase Activation and Fas Upregulation," *J. Clin. Invest*.102:2041–2049, The American Society for Clinical Investigation, Inc., New York, NY (Dec. 1998).

del pozo, O., and Lam, E., "Caspases and programmed cell death in the hypersensitive response of plants to pathogens," *Curr. Biol*. 8:1129–1132, Current Biology Ltd., London England (Oct. 1998).

di Giovine, F.S., and Duff, G.W., "Interleukin 1: the first interleukin," *Immunology Today* 11:13–14, Elsevier Science Publishers Ltd., Barking, England (1990).

Dinarello, C. A., "Interleukin–1 and Interleukin–1 Antagonism," *Blood* 77:1627–1652, American Society for Hematology, Philadelphia, PA (1991).

(List continued on next page.)

Primary Examiner—Christopher S. F. Low
Assistant Examiner—Chih-Min Kam
(74) Attorney, Agent, or Firm—Sterne, Kessler, Goldstein & Fox P.L.L.C.

(57) ABSTRACT

The use of caspase inhibitors for treating, ameliorating, and preventing non-cancer cell death during chemotherapy and radiation therapy and for treating and ameliorating the side effects of chemotherapy and radiation therapy of cancer is disclosed.

19 Claims, 9 Drawing Sheets

OTHER PUBLICATIONS

Dolle, R.E. et al., "$P_1$ Aspartate–Based Peptide α–((2, 6–Dichlorobenzoyl)oxy) methyl Ketones as Potent Time Dependent Inhibitors of Interleukin–1β–Converting Enzyme," *J. Med. Chem.* 37:563–564, American Chemical Society, Washington, DC (1994).

Dolle, R.E. et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme– Peptide Inhibitor Binding," *J. Med. Chem.* 37:3863–3866, American Chemical Society, Washington, DC (1994).

Dolle R.E. et al., "Aspartyl α–((Diphenylphosphinyl)oxy)methyl Ketones as Novel Inhibitors of Interleukin–1β Converting Enzyme. Utility of the Diphenylphosphinic Acid Leaving Group for the Inhibition of Cysteine Proteases," *J. Med. Chem.* 38:220–222, American Chemical Society, Washington, DC (1995).

Ellis, R.E. et al., "Mechanisms and Fuctions of Cell Death," *Ann. Rev. Cell Bio.* 7:663–698, Annual Reviews, Palo Alto, CA (1991).

Emery, E. et al., "Apoptosis after traumatic human spinal cord injury," *J. Neurosurg.* 89:911–920, American Association of Neurological Surgeons, Charlottesville, VA (Dec. 1998).

Goldberg, Y.P et al., "Cleavage of huntingtin by apopain, a proapoptotic cysteine protease, is modulated by the polyglutamine tract," *Nature Genetics* 13:442–449, Nature Publishing Co., New York, NY (1996).

Graybill, T.L. et al., "α–((Tetronoyl)oxy)– and α–((Tetramoyl)oxy)methyl Ketone Inhibitors of the interleukin–1β Converting Enzyme (ICE)," *Bioorg. Med. Chem. Lett.* 7:41–46, Elsevier Science Ltd., Oxford, England (1997).

Greenberg, J.T. et al., "Programmed Cell Death in Plants: A Pathogen–Triggered Response Activated Coordinately with Multiple Defense Functions," *Cell* 77:551–563, Cell Press, Cambridge, MA (1994).

Grombyer, S.R. et al., "Peptidomimetic Fluoromethylketone Rescues Mice from Lethal Endotoxic Shock," *Mol Med.* 5:585–594, Johns Hopkins University Press, Baltimore, MD (Sep. 1999).

Hara, H. et al., "Inhibition of interleukin 1β converting enzyme family proteases reduces Ischemic and excitotoxic neuronal damage," *Proc. Natl. Acad. Sci. USA* 94:2007–2012. National Academy of Sciences, Washington, DC (Mar. 1997).

Hiraoka, J. et al., "Participation of apoptosis in renal amyloidosis," *Jpn. J. Nephrol.* 40:276–283, Japanese Society of Nephrology, Tokyo, Japan (May 1998).

Hotchkiss, R.S. et al., "Prevention of lymphocyte cell death is sepsis improves survival in mice," *Proc. Natl. Acad. Sci. USA* 96:14541–14546, National Academy of Sciences, Washington, DC (Dec. 1999).

Jaeschke, H. et al., "Activation of Caspase 3 (CPP32)–Like Proteases Is Essential for TNF–α–Induced Hepatic Parenchymal Cell Apoptosis and Neutrophil–Mediated Necrosis in a Murine Endotoxin Shock Model," *J. Immun.* 160:3480–3486, American Association of Immunologists, Baltimore, MD (Apr. 1998).

Jones, R. A. et al., "Fas–Mediated Apoptosis in Mouse Hepatocytes Involves the Processing and Activation of Caspases," *Hepatology* 27:1632–1642, American Association for the Study of Liver Diseases, Philadelphia, PA (Jun. 1998).

Kermer, P. et al., "Inhibition of CPP32–Like Proteases Rescues Axotomized Retinal Ganglion Cells from Secondary Cell Death In Vivo," *J. Neuroscience* 18:4656–4662, Society for Neuroscience, Washington, DC (Jun. 1998).

Kubo, S. et al., "Hepatocyte injury in tyrosinemia type 1 is induced by fumarylacetoacetate and is inhibited by caspase inhibitors," *Proc. Natl. Acad. Sci. USA* 95:9552–9557, National Academy of Sciences, Washington, DC (Aug. 1998).

Lepschy, J., "Acylierung von Oxazolinonen–(5) unter besonderer Berücksichtigung der Dakin–west–Reaktion trifunktioneller Aminosäuren," *Ph.D. Thesis*, Technischen Universität München (1971).

Lieberthal, W. et al., "Necrosis and Apoptosis in Acute Renal Failure," *Sem. Nephr.* 18:505–518, W.B. Saunders Company, Philadelphia, PA (Sep. 1998).

Lotem, J. and Sachs, L., "Differential suppression by protease inhibitors and cytokines of apoptosis induced by wild–type p53 and cytotoxic agents," *Proc. Natl. Acad. Sci. USA* 93:12507–12512, National Academy of Sciences, Washington, DC (1996).

Mattson, M.P. et al., "Amyloid β–peptide includes apoptosis–related events in synapses and dendrites," *Brain Res.* 807:167–176, Elsevier Science B.V., Amsterdam, Netherlands (Oct. 1998).

Maulik, N. et al., "Oxidative stress developed during the reperfusion of ischemic myocardium induces apoptosis," *Free Rad. Biol. & Med.* 24:869–875, Elsevier Science Inc., Tarrytown, NY (Mar. 1998).

Miller, P.E. et al., "Photoreceptor cell death by apoptosis in dogs with sudden acquired retinal degeneration syndrome" *Am. J. Vet. Res.* 59:149–152, American Veterinary Medical Association, Schaumburg, IL (Feb. 1998).

Miura, M. et al., "Induction of Apoptosis in Fibroblasts by IL–1β–Converting Enzyme, a Mammalian Homolog of the *C. elegans* Cell Death Gene ced–3," *Cell* 75:653–660, Cell Press, Cambridge, MA (1993).

Mjalli, A.M.M. et al., "Phenylalkyl Ketones as Potent Reversible Inhibitors of Interleukin–1β Converting Enzyme," *Bioorg. Med. Chem. Lett.* 3:2689–2692, Elsevier Science Ltd., Oxford, England (1993).

Mjalli, A.M.M. et al., "Activated Ketones as Potent Reversible Inhibitors of Interleukin–1β Converting Enzyme," *Bioorg. Med. Chem. Lett.* 4:1965–1968, Elsevier Science Ltd., Oxford, England (1994).

Mjalli, A.M.M. et al., "Inhibition of Interleukin–1β Converting Enzyme by N–acyl–aspartic acid Ketones," *Bioorg. Med. Chem. Lett.* 5:1405–1408 Elsevier Science Ltd., Oxford, England (1995).

Mjalli, A.M.M. et al., "Inhibition of Interleukin–1β Converting Enzyme by N–acyl–aspartic acid Ketones," *Bioorg. Med. Chem. Lett.* 5:1409–1414, Elsevier Science Ltd., Oxford, England (1995).

Mosley, B. et al., "The Interleukin–1 Receptor Binds the Human Interleukin–1α Precursor but Not the Interleukin–1β Precursor," *J. Biol. Chem.* 262:2941–2944, American Society of Biological Chemists, Inc., Baltimore, MD (1987).

Mundle, S. D. et al., "Evidence for Involvement of Tumor Necrosis Factor–α in Apoptotic Death of Bone Marrow Cells in Myelodysplastic Syndromes," *Am. J. Hemat.* 60:36–47, Wiley–Liss, Inc., New York, NY (Jan. 1999).

Okamoto, Y. et al., "Peptide Based Interleukin–1β Converting Enzyme (ICE) Inhibitors: Synthesis, Structure Activity Relationships and Crystallographic Study of the ICE–inhibitor Complex," *Chem. Pharm. Bull.* 47:11–21, Pharmaceutical Society of Japan (1991).

Oppenheim, J. J. et al., "There is more than one interleukin–1," *Immun. Today* 7:45–56, Elsevier Science Publishers B.V., Amsterdam, Netherlands (1986).

Orrenius, S., "Apoptosis: molecular mechanism and implications for human disease," *J. Internal Medicine* 237:529–536, Blackwell Science Ltd., Oxford, England (1995).

Ortiz, A. et al., "Cyclosporine A induces apoptosis in murine tubular epithelial cells: Role of caspases," *Kidney Int'l.* 54:S–25—S–29, International Society of Nephrology, Amsterdam, Netherlands (Dec. 1998).

Peleg, S. et al., "1,25–Dihydroxyvitamin $D_3$ and its analogs inhibit acute myelogenous leukemia progenitor Proliferation by suppressing interleukin–1β production," *Chemical Abstracts 127*, Abstract No. 315124p, American Chemical Society, Washington DC (1997).

Rasnick, D., "Synthesis of Peptide Fluoromethyl Ketones and the Inhibition of Human Cathepsin B," *Anal. Biochem.* 149:461–465, Academic Press, New York, NY (1985).

Rauber, P. et al., "The synthesis of peptidylfluromethanes and their properties as inhibitors of serine proteinases and cysteine proteinases," *Biochem J.* 239:633–640, The Biochemical Society, London, England (1986).

Revesz, L. et al., "Synthesis of P1 Aspartate–Based Acyloxymethyl and Fluromethyl Ketones as Inhibitors of Interleukin–1β–Converting Enzyme," *Tet. Lett.* 35:9693–9696, Elsevier Science Ltd., United Kingdom (1994).

Rich, D.H., "Inhibitors of aspartic proteinases," in *Proteinase inhibitors. Research monographs in cell and tissue physiology.* vol. 12, Barrett, A.J. and G. Salvesen, eds., Elsevier, Amsterdam, Holland, pp. 179–208 (1986).

Richberg, M.H. et al., "Dead cells to tell tales," *Curr. Op. Plant Bio.* 1:480–485, Elsevier Science Ltd., United Kingdom (Dec. 1998).

Rodriguez, I. et al., "Systemic Injection of a Tripeptide Inhibits the Intracellular Activation of CPP32–like Proteases In Vivo and Fully Protects Mice against Fas–mediated Fulminant Liver Destruction and Death," *J. Exp. Med.* 184:2067–2072, The Rockfeller University Press, New York, NY (1996).

Semple, G. et al., "Peptidomimetic Aminomethylene Ketone Inhibitors of Interleukin–1β–Converting Enzyme (ICE)," *Bioorg. Med. Chem. Lett.* 8:959–964, Elsevier Science Ltd., Oxford, England (1998).

Shaw, E. et al., "Peptidyl fluoromethyl ketones as thiol protease inhibitors," *Biomed. Biochim., Acta* 45:1397–1403, Academie Verlag, Berlin, Germany (1986).

Sheikh, M.S. et al., "Ultraviolet–irradiation–induced apoptosis is mediated via ligand independent activation of tumor necrosis factor receptor 1," *Oncogene* 17:2555–2563, Stockton Press, London, England (Nov. 1998).

Sleath, P.R. et al., "Substrate Specificity of the Protease That Processes Human Interleukin–1β," *J. Bio. Chem.* 265:14526–14528, American Society for Biochemistry and Molecular Biology, Inc., Baltimore, MD (1990).

Slomiany, B.L. et al., "Activation of Apoptotic Caspase–3 and Nitric Oxide Synthase–2 in Buccal Mucosa with Chronic Alcohol Ingestion," *Biochem. & Mol. Bio. Int'l.* 45:1199–1209, Academic Press, Sydney, Australia (Sep. 1998).

Steinberg, D., "Caspase Inhibitors. Molecules Sought For Treatment of Diverse Disorders," *Gen. Eng. News* 18:16, 38,51, Mary Ann Liebert, Inc., New York, NY (Jul. 1998).

Suzuki, A., "The Dominant Role of CPP32 Subfamily in Fas–Mediated Hepatitis," *Proc. Soc. Exp. Biol. Med.* 217:450–454, Society for Experimental Biology and Medicine, Cambridge, MA (Apr. 1998).

Thornberry, N.A. et al., "A novel heterodimeric cysteine protease is required for interleukin–1β processing in monocytes," *Nature* 356:768–774, Nature Publishing Group, London, England (1992).

Thornberry, N.A. et al., "A Combinatorial Approach Defines Specificities of Members of the Caspase Family and Granzyme B," *J. Biol. Chem.* 272:17907–17911, American Society for Biochemistry and Molecular Biology, Inc., Baltimore, MD (1997).

Thornberry, N.A. "Caspases: key mediators of apoptosis," *Chem. Biol.* 5:R97–R103, Current Biology Ltd., London, England (May 1998).

Thornberry, N.A. et al., "Inactivation of Interleukin–1β Converting Enzyme by Peptide (Acyloxy)methyl Ketones," *Biochemistry* 33:3934–3940, American Chemical Society, Washington, DC (1994).

Wataya, Y. et al., "Cytotoxic mechanism of 1–(3–C–ethynyl– β–D–ribo–pentofuranosyl) cytosine (ECyd)," *Chemical Abstracts 132*, Abstract No. 273983p, American Chemical Society, Washington, DC (May 2000).

Weil, M. et al., "Is programmed cell death required for neural tube closure?" *Curr. Biol.* 7:281–284, Current Biology Ltd., London, England (Apr. 1997).

Wyllie, A.H. et al., "Cell Death: The Significance of Apoptosis," *Int. Rev. Cyt.* 68:251–306, Academic Press, Inc., New York, NY (1980).

Wyllie, A.H. et al., "Cell death: a new classifciation separating apoptosis from necrosis," in *Cell Death in Biology and Pathology*, Bowen and Lockin, eds., Chapman and Hall, New York, NY, pp. 9–34 (1981).

Xue, D. et al., "The Time Course for Infarction in a Rat Model of Transient Focal Ischemia," *Stroke* 21:166, Abstract No. 36, American Heart Association, Baltimore, MD (1990).

Yuan, J. et al., "The *C. elegans* Cell Death Gene ced–3 Encodes a Protein Similar to Mammalian Interleukin–1β–Converting Enzyme," *Cell* 75:641–652, Cell Press, Inc., Cambridge, MA (1993).

Cai, S.X. et al., U.S. patent application Ser. No. 09/527,225, filed Mar. 16, 2000.

Cai, S.X. et al., U.S. patent application Ser. No. 09/545,565, filed Apr. 7, 2000.

Wang, Y. et al., U.S. patent application Ser. No. 09/649,810, filed Aug. 28, 2000.

Keana, J. F. W. et al., U.S. patent application Ser. No. 09/653,279, filed Aug. 31, 2000.

English language abstract for JP 11–180891, Derwent World Patents Index Accession No. 1999–439401.

International Search Report for International Application No. PCT/US00/28069, mailed Feb. 28, 2001.

Derwent Database, WPI Accession No. 1999–439401, English language abstract of JP 11180891 (1999).

* cited by examiner

CASPASE INHIBITORS FOR THE TREATMENT AND PREVENTION OF CHEMOTHERAPY AND RADIATION THERAPY INDUCED CELL DEATH

CROSS-REFERENCE TO RELATED APPLICATIONS

This application claims the benefit of U.S. Provisional Application No. 60/187,868, filed March 8, 2000, and U.S. Provisional Application No. 60/158,385, filed Oct. 12, 1999, the contents of which are entirely incorporated by reference herein.

BACKGROUND OF THE INVENTION

1. Field of the Invention

This invention is in the field of medicinal chemistry. In particular, the invention relates to the use of caspase inhibitors to treat or prevent non-cancer cell death during chemotherapy and radiation therapy of cancer.

2. Description of Background Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis et al., *Dev.* 112:591–603 (1991); Vaux et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO6/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wylie et al., *Int. Rev. Cyt.* 68: 251 (1980); Ellis et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

Mammalian interleukin-1β (IL-1β) plays an important role in various pathologic processes, including chronic and acute inflammation and autoimmune diseases (Oppenheim, J. H. et. al. *Immunology Today*, 7, 45–56 (1986)). IL-1β is synthesized as a cell associated precursor polypeptide (pro-IL-1β) that is unable to bind IL-1 receptors and is biologically inactive (Mosley et al., *J. Biol. Chem.* 262:2941–2944 (1987)). By inhibiting conversion of precursor IL-1β to mature IL-1β, the activity of interleukin-1 can be inhibited. Interleukin-1β converting enzyme (ICE) is a protease responsible for the activation of interleukin-1β (IL-1β) (Thornberry, N. A., et al., *Nature* 356: 768 (1992); Yuan, J., et al., *Cell* 75: 641 (1993)). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICHl, TX/ICH-2, MCH2, MCH3, MCH4, FLICE/MACH/MCH5, ICE-LAP6 and $ICE_{rel}III$. The proteolytic activity of this family of cysteine proteases, whose active site (a cysteine residue) is essential for ICE-mediated apoptosis, appears critical in mediating cell death (Miura et al., *Cell* 75: 653–660 (1993)). This gene family has recently been named caspases (Alnernri, E. S. et. al. *Cell*, 87, 171 (1996), and Thomberry, N. A. et. al. *J. Biol. Chem.* 272, 17907–17911 (1997)) and divided into three groups according to its known functions. Table 1 summarizes these known caspases.

TABLE 1

Enzyme*

Group I: mediators of inflammation
Caspase-1 (ICE)
Caspase-4 ($ICE_{rel}$-II, TX, ICH-2)
Caspase-5 ($ICE_{rel}$-III, TY)
Group II: effectors of apoptosis
Caspase-2 (ICH-1, mNEDD2)
Caspase-3 (apopain, CPP-32, YAMA)
Caspase-7 (Mch-3, ICE-LAP3, CMH-1)
Group III: activators of apoptosis
Caspase-6 (Mch2)
Caspase-8 (MACH, FLICE, Mch5)
Caspase-9 (ICE-LAP6, Mch6)
Caspase-10

IL-1 is also a cytokine involved in mediating a wide range of biological responses including inflammation, septic shock, wound healing, hematopoiesis and growth of certain leukemias (Dinarello, C. A., *Blood* 77:1627–1652 (1991); diGiovine et al., *Immunology Today* 11:13 (1990)).

WO 93/05071 discloses peptide ICE inhibitors with the formula:

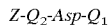

wherein Z is an N-terminal protecting group; $Q_2$ is 0 to 4 amino acids such that the sequence $Q_2$-Asp corresponds to at least a portion of the sequence Ala-Tyr-Val-His-Asp; $Q_1$ comprises an electronegative leaving group.

WO 96/03982 discloses aspartic acid analogs as ICE inhibitors with the formula:

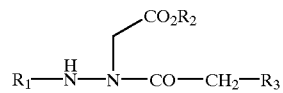

wherein $R_2$ is H or alkyl; $R_3$ is a leaving group such as halogen; $R_1$ is heteroaryl-CO or an amino acid residue.

U.S. Pat. No. 5,585,357 discloses peptidic ketones as ICE inhibitors with the formula:

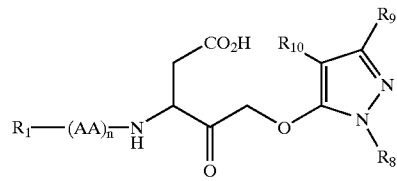

wherein n is 0–2; each AA is independently L-valine or L-alanine; $R_1$ is selected from the group consisting of N-benzyloxycarbonyl and other groups; $R_8, R_9, R_{10}$ are each independently hydrogen, lower alkyl and other groups.

Mjalli et al. (*Bioorg. Med. Chem. Lett.*, 3, 2689–2692, 1993) report the preparation of peptide phenylalkyl ketones as reversible inhibitors of ICE, such as:

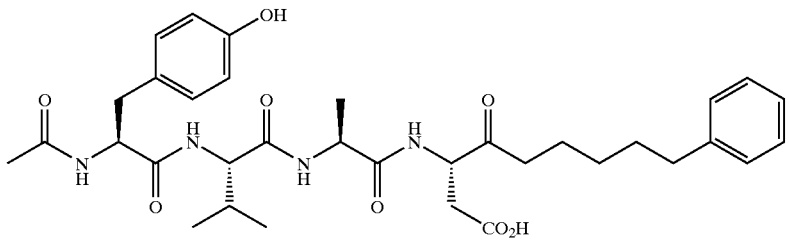

Thornberry et al. (*Biochemistry*, 33, 3934–3940, 1994) report the irreversible inactivation of ICE by peptide acyloxymethyl ketones:

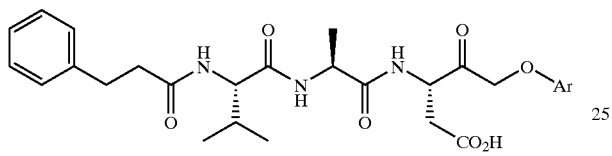

wherein Ar is $COPh\text{-}2,6\text{-}(CF_3)_2$, $COPh\text{-}2,6\text{-}(CH_3)_2$, $Ph\text{-}F_5$ and other groups.

Dolle et al. (*J. Med. Chem.* 37, 563–564, 1994) report the preparation of $P_1$ aspartate-based peptide α-((2,6-dichlorobenzoyl)oxy)methyl ketones as potent time-dependent inhibitors of ICE, such as:

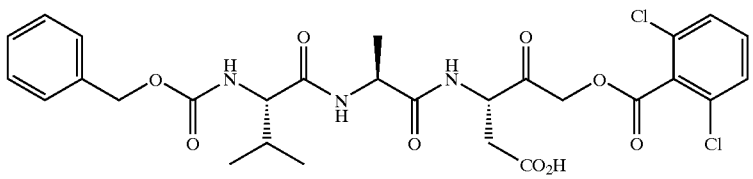

Mjalli et al. (*Bioorg. Med. Chem. Lett.*, 4, 1965–1968, 1994) report the preparation of activated ketones as potent reversible inhibitors of ICE:

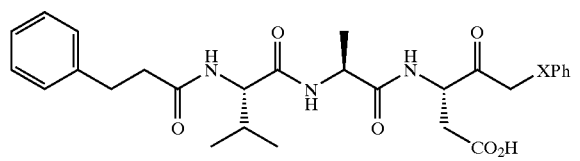

wherein X is $NH(CH_2)_2$, $OCO(CH_2)_2$, $S(CH_2)_3$ and other groups.

Dolle et al. (*J. Med. Chem.* 37, 3863–3866, 1994) report the preparation of α-((1-phenyl-3-(trifluoromethyl)-pyrazol-5-yl)oxy)methyl ketones as irreversible inhibitor of ICE, such as:

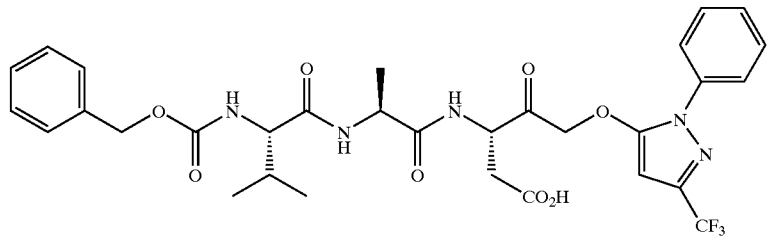

Mjalli et al. (*Bioorg. Med. Chem. Lett.*, 5, 1405–1408, 1995) report inhibition of ICE by N-acyl-Aspartic acid ketones:

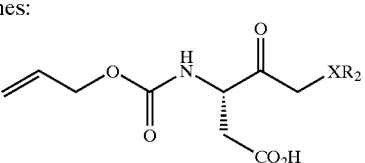

wherein $XR_2$ is $NH(CH_2)_2Ph$, $OCO(CH_2)_2cyclohexyl$ and other groups.

Mjalli et al. (*Bioorg. Med. Chem. Lett.*, 5, 1409–1414, 1995) report inhibition of ICE by N-acyl-aspartyl aryloxymethyl ketones, such as:

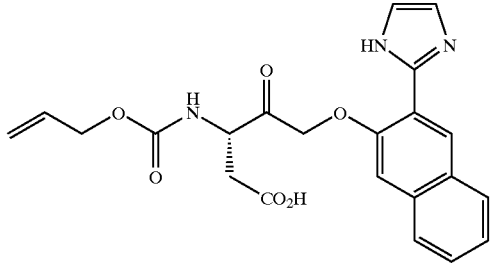

Dolle et al. (*J. Med. Chem.* 38, 220–222, 1995) report the preparation of aspartyl α-((diphenylphosphinyl)oxy)methyl ketones as irreversible inhibitors of ICE, such as:

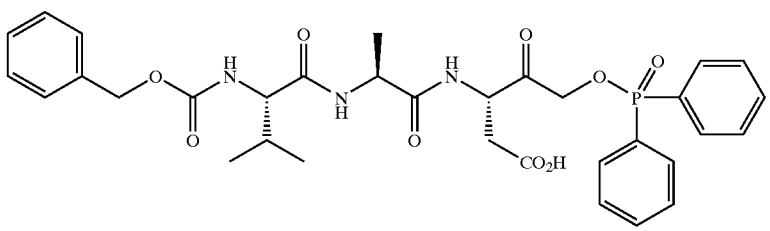

Graybill et al. (*Bioorg. Med. Chem. Lett.*, 7, 41–46, 1997) report the preparation of α-((tetronoyl)oxy)- and α-((tetramoyl)oxy)methyl ketones as inhibitors of ICE, such as:

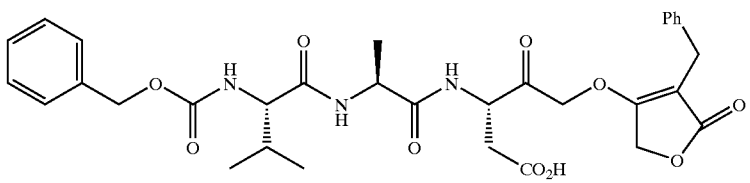

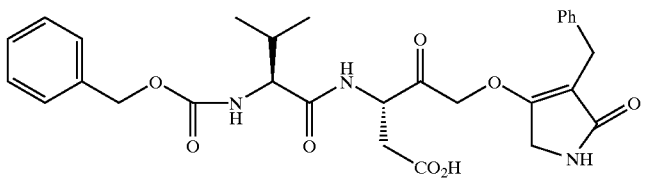

Semple et al. (*Bioorg. Med. Chem. Lett.*, 8, 959–964, 1998) report the preparation of peptidomimetic aminomethylene ketones as inhibitors of ICE, such as:

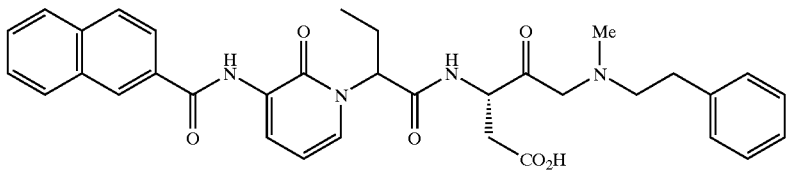

Okamoto et al. (*Chem. Pharm. Bull.* 47, 11–21, 1999) report the preparation of peptide based ICE inhibitors with the P1 carboxyl group converted to an amide, such as:

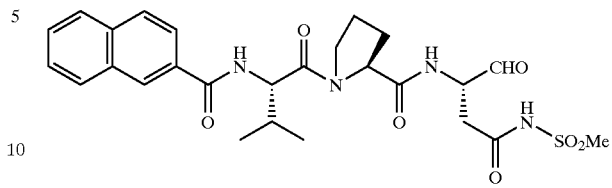

EP618223 patent application disclosed inhibitor of ICE as anti-inflammatory agents:

$$R\text{-}A_1\text{-}A_2\text{-}X\text{-}A_3$$

Wherein R is a protecting group or optionally substituted benzyloxy; $A_1$ is an α-hydroxy or α-amnino acid residue or a radical of formula:

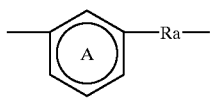

wherein ring A is optionally substituted by hydroxy or $C_{1-4}$ alkoxy and $R_a$ is CO or CS; $A_2$ is an α-hydroxy or α-amino acid residue or $A_1$ and $A_2$ form together a pseudo-dipeptide or a dipeptide mimetic residue; X is a residue derived from Asp; $A_3$ is —$CH_2$—$X_1$—CO—$Y_1$, —$CH_2$—O—$Y_2$, —$CH_2$—S—$Y_3$, wherein $X_1$ is O or S; $Y_1$, $Y_2$ or $Y_3$ is cycloaliphatic residue, and optionally substituted aryl.

WO99/18781 and U.S. Application Ser. No. 09/168,945 disclose dipeptides of formula I:

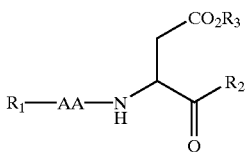

wherein $R_1$ is an N-terminal protecting group; AA is a residue of any natural or non-natural α-amino acid, β-amino acid, derivatives of an α-amino acid or β-amino acid; $R_2$ is H or $CH_2R_4$ where R4 is an electronegative leaving group, and $R_3$ is alkyl or H, provided that AA is not His, Tyr, Pro or Phe. These dipeptides are surprisingly potent caspase inhibitors of apoptosis in cell based systems. These compounds are systemically active in vivo and are potent inhibitors of antiFas-induced lethality in a mouse liver apoptosis model and have robust neuroprotective effects in a rat model of ischemic stroke. Exemplary preferred inhibitors of apoptosis include Boc-Ala-Asp-$CH_2F$, Boc-Val-Asp-$CH_2F$, Boc-Leu-Asp-$CH_2F$, Ac-Val-Asp-$CH_2F$, Ac-Ile-Asp-$CH_2F$, Ac-Met-Asp-$CH_2F$, Cbz-Val-Asp-$CH_2F$, Cbz-β-Ala-Asp-$CH_2F$, Cbz-Leu-Asp-$CH_2F$, Cbz-Ile-Asp-$CH_2F$, Boc-Ala-Asp(OMe)-$CH_2F$, Boc-Val-Asp(OMe)-$CH_2F$, Boc-Leu-Asp(OMe)-$CH_2F$, Ac-Val-Asp(OMe)-$CH_2F$, Ac-Ile-Asp(OMe)-$CH_2F$, Ac-Met-Asp(OMe)-$CH_2F$, Cbz-Val-Asp(OMe)-$CH_2F$, Cbz-β-Ala-Asp(OMe)-$CH_2F$, Cbz-Leu-Asp(OMe)-$CH_2F$ and Cbz-Ile-Asp(OMe)-$CH_2F$.

WO 99/47154 and U.S. Application Ser. No. 09/270,735 disclose dipeptides of formula II:

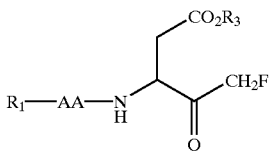

wherein $R_1$ is an N-terminal protecting group; AA is a residue of a non-natural α-amino acid or β-amino acid; $R_2$ is an optionally substituted alkyl or H. Exemplary inhibitors of caspases and apoptosis include Boc-Phg-Asp-fmk, Boc-(2-F-Phg)-Asp-fmk, Boc-($F_3$-Val)-Asp-fmk, Boc-(3-F-Val)-Asp-fmk, Ac-Phg-Asp-fmk, Ac-(2-F-Phg)-Asp-fmk, Ac-($F_3$-Val)-Asp-fmk, Ac-(3-F-Val)-Asp-fmk, Z-Phg-Asp-fmk, Z-(2-F-Phg)-Asp-fmk, Z-($F_3$-Val)-Asp-frnk, Z-Chg-Asp-fmk, Z-(2-Fug)-Asp-fmk, Z-(4-F-Phg)-Asp-fmk, Z-(4-Cl-Phg)-Asp-fmk, Z-(3-Thg)-Asp-fmk, Z-(2-Fua)-Asp-fmk, Z-(2-Tha)-Asp-fmk, Z-(3-Fua)-Asp-fmk, Z-(3-Tha)-Asp-fmk, Z-(3-Cl-Ala)-Asp-fmk, Z-(3-F-Ala)-Asp-fmk, Z-($F_3$-Ala)-Asp-fmk, Z-(3-F-3-Me-Ala)-Asp-fmk, Z-(3-Cl-3-F-Ala)-Asp-fmk, Z-(2-Me-Val)-Asp-fmk, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-(3-$CF_3$-Ala)-Asp-fmk, Z-(4-$CF_3$-Phg)-Asp-fmk, Z-(3-$Me_2$N-Ala)-Asp-fmk, Z-(2-Abu)-Asp-fmk, Z-Tle-Asp-fmk, Z-Cpg-Asp-fmk, Z-Cbg-Asp-fmk, Z-Thz-Asp-fmk, Z-(3-F-Val)-Asp-fmk, and Z-(2-Thg)-Asp-fmk; where Z is benzyloxycarbonyl, BOC is tert.-butoxycarbonyl, Ac is acetyl, Phg is phenylglycine, 2-F-Phg is (2-fluorophenyl) glycine, $F_3$-Val is 4,4,4-trifluoro-valine, 3-F-Val is 3-fluoro-valine, 2-Thg is (2-thienyl)glycine, Chg is cyclohexylglycine, 2-Fug is (2-furyl)glycine, 4-F-Phg is (4-fluorophenyl)glycine, 4-Cl-Phg is (4-chlorophenyl) glycine, 3-Thg is (3-thienyl)glycine, 2-Fua is (2-furyl) alanine, 2-Tha is (2-thienyl)alanine, 3-Fua is (3-furyl) alanine, 3-Tha is (3-thienyl)alanine, 3-Cl-Ala is 3-chloroalanine, 3-F-Ala is 3-fluoroalanine, $F_3$-Ala is 3,3,3-trifluoroalanine, 3-F-3-Me-Ala is 3-fluoro-3-methylalanine, 3-Cl-3-F-Ala is 3-chloro-3-fluoroalanine, 2-Me-Val is 2-methylvaline, 2-Me-Ala is 2-methylalanine, 2-i-Pr-β-Ala is 3-amino-2-isopropylpropionic acid, 3-Ph-β-Ala is 3-amino-3-phenylpropionic acid, 3-CN-Ala is 3-cyanoalanine, 1-Nal is 3-(1-naphthyl)-alanine, Cha is cyclohexylalanine, 3-$CF_3$-Ala is 2-amino4,4,4-trifluorobutyric acid, 4-$CF_3$-Phg is 4-trifluoromethyl-phenylglycine, 3-$Me_2$N-Ala is 3-dimethylamino-alanine, 2-Abu is 2-aminobutyric acid, Tle is tert-leucine, Cpg is cyclopentylglycine, Cbg is cyclobutylglycine, and Thz is thioproline.

SUMMARY OF THE INVENTION

The invention arises out of the discovery that caspase inhibitors are very effective in preventing cell death induced by radiation and anticancer drugs. The invention thus relates to the use of caspase inhibitors for treating, ameliorating, and preventing non-cancer cell death during chemotherapy and radiation therapy and for treating and ameliorating the side effects of chemotherapy and radiation therapy of cancer.

In particular, the invention relates to a method of treating, ameliorating or preventing oral mucositis, gastrointestinal mucositis, bladder mucositis, proctitis, bone marrow cell death, skin cell death and hair loss resulting from chemotherapy or radiation therapy of cancer in an animal, comprising administering to the animal in need thereof an effective amount of a caspase inhibitor.

DETAILED DESCRIPTION OF THE INVENTION

Figure 1A:
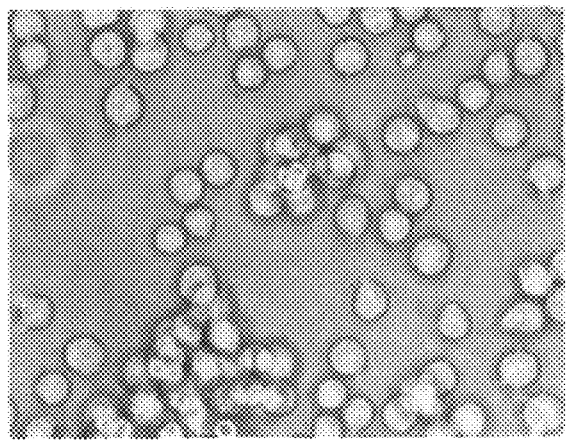
FIGS. 1A–C depict photographs of Jurkat cells.

The invention relates to a method of treating, ameliorating or preventing oral mucositis, gastrointestinal mucositis, bladder mucositis, proctitis, bone marrow cell death, skin cell death and hair loss resulting from chemotherapy or radiation therapy of cancer in an animal, comprising administering to the animal in need thereof an effective amount of a caspase inhibitor.

When animals are treated with chemotherapeutic agents and/or radiation to kill cancer cells, an unwanted side effect is the apoptotic death of rapidly dividing non-cancer cells. Such non-cancer cells include cells of the gastrointestinal tract, skin, hair, and bone marrow cells. According to the present invention, caspase inhibitors are administered to such non-cancer cells to prevent apoptosis of such cells. In a preferred embodiment, the caspase inhibitors are administered locally, e.g. to the gastrointestinal tract, mouth, skin or scalp to prevent apoptosis of the gastrointestinal, mouth, skin or hair cells but allowing for the death of the cancer cells. Thus, in one example, it is possible to treat brain cancer with chemotherapy or radiation therapy and protect the outer skin, hair cells, gastrointestinal tract and bone marrow by local administration of a caspase inhibitor. In the case of oral mucositis, the caspase inhibitor can be applied, for example, in the form of a mouth wash or mouth rinse, in a gel, or in the form of an oral slow release lozenge to prevent activation of caspases and apoptotic cell death induced by the chemotherapeutic agent or by radiation. In the case of gastrointestinal mucositis, the caspase inhibitor can be applied in a form such that it is not absorbed systemically or in a form that coats the surface of the gastrointestinal tract, or a suppository formulation for the treatment of gastrointestinal mucositis. In the case of proctitis, the capsase inhibitor may be applied as part of an enema or suppository. In the case of bladder mucositis, the caspase inhibitor may be applied though a bladder catheter. For prevention of radiation or chemotherapy-induced hair loss, the caspase inhibitor can be applied, for example, to the scalp in the form of a hair rinse, hair gel, shampoo or hair conditioner. Importantly, the caspase inhibitor can be applied prior to the administration of the chemotherapeutic agent or radiation, thus preventing the onset of the damaging effects of the chemotherapeutic agent or radiation to the normal cells.

In a preferred embodiment, the caspase inhibitor has the formula:

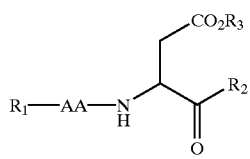

I or a pharmaceutically acceptable salt thereof;
wherein $R_1$ is an N-terminal protecting group;
AA is a residue of any natural or non-natural α-amino acid, β-amino acid, derivatives of an α-amino acid or β-amino acid;
$R_2$ is H or $CH_2R_4$ where $R_4$ is an electronegative leaving group; and
$R_3$ is alkyl or H.

Examples of such caspase inhibitors include Boc-Ala-Asp-$CH_2F$, Boc-Val-Asp-$CH_2F$, Boc-Leu-Asp-$CH_2F$, Ac-Val-Asp-$CH_2F$, Ac-Ile-Asp-$CH_2F$, Ac-Met-Asp-$CH_2F$, Cbz-Val-Asp-$CH_2F$, Cbz-β-Ala-Asp-$CH_2F$, Cbz-Leu-Asp-$CH_2F$, Cbz-Ile-Asp-$CH_2F$, Boc-Ala-Asp(OMe)-$CH_2F$, Boc-Val-Asp(OMe)-$CH_2F$, Boc-Leu-Asp(OMe)-$CH_2F$, Ac-Val-Asp(OMe)-$CH_2F$, Ac-Ile-Asp(OMe)-$CH_2F$, Ac-Met-Asp(OMe)-$CH_2F$, Cbz-Val-Asp(OMe)-$CH_2F$, Cbz-β-Ala-Asp(OMe)-$CH_2F$, Cbz-Leu-Asp(OMe)-$CH_2F$ or Cbz-Ile-Asp(OMe)-$CH_2F$.

In another preferred embodiment, the caspase inhibitor has the formula II:

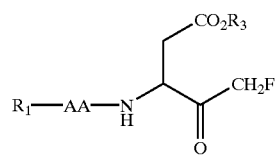

II or a pharmaceutically acceptable salt thereof;
wherein $R_1$ is an N-terminal protecting group;
AA is a residue of a non-natural α-amino acid or β-amino acid; and
$R_2$ is an optionally substituted alkyl or H.

Examples of such caspase inhibitors include Boc-Phg-Asp-fmk, Boc-(2-F-Phg)-Asp-fmk, Boc-($F_3$-Val)-Asp-fmk, Boc-(3-F-Val)-Asp-fmk, Ac-Phg-Asp-fmk, Ac-(2-F-Phg)-Asp-fmk, Ac-($F_3$-Val)-Asp-fmk, Ac-(3-F-Val)-Asp-fmk, Z-Phg-Asp-fmk, Z-(2-F-Phg)-Asp-fmk, Z-($F_3$-Val)-Asp-fmk, Z-Chg-Asp-fmk, Z-(2-Fug)-Asp-fmk, Z-(4-F-Phg)-Asp-fmk, Z-(4-Cl-Phg)-Asp-fmk, Z-(3-Thg)-Asp-fmk, Z-(2-Fua)-Asp-fmk, Z-(2-Tha)-Asp-fmk, Z-(3-Fua)-Asp-fmk, Z-(3-Tha)-Asp-fmk, Z-(3-Cl-Ala)-Asp-fmk, Z-(3-F-Ala)-Asp-fmk, Z-($F_3$-Ala)-Asp-fmk, Z-(3-F-3-Me-Ala)-Asp-fmk, Z-(3-Cl-3-F-Ala)-Asp-fmk, Z-(2-Me-Val)-Asp-fmk, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-(3-$CF_3$-Ala)-Asp-fmk, Z-(4-$CF_3$-Phg)-Asp-fmk, Z-(3-$Me_2$N-Ala)-Asp-fmk, Z-(2-Abu)-Asp-fmk, Z-Tle-Asp-fmk, Z-Cpg-Asp-fmk, Z-Cbg-Asp-fmk, Z-Thz-Asp-fmk, Z-(3-F-Val)-Asp-fmk, and Z-(2-Thg)-Asp-fmk.

Other caspase inhibitors that may be used in the practice of the invention include without limitation those described in WO93/05071, WO93/09135, WO93/14777, WO95/26958, WO95/29672, WO95/33751, WO96/03982, WO96/30395, WO97/07805, WO97/08174, WO97/22618, WO97/27220, WO98/11109, WO98/11129, WO98/16502, WO98/16504, WO98/16505, WO98/24804, WO98/24805, EP 519748, EP 547699, EP 618223, EP 623592, EP623606, EP 628550, EP 644198, U.S. Pat. No. 5,430,128, U.S. Pat. No. 5,434,248, U.S. Pat. No. 5,462,939, U.S. Pat. No. 5,552,400, U.S. Pat. No. 5,565,430, U.S. Pat. No. 5,585,357, U.S. Pat. No. 5,585,486, U.S. Pat. No. 5,622,967, U.S. Pat. No. 5,639,745, U.S. Pat. No. 5,656,627, U.S. Pat. No. 5,670,494, U.S. Pat. No. 5,677,283, U.S. Pat. No. 5,716,929, U.S. Pat. No. 5,739,279, U.S. Pat. No. 5,756,465, U.S. Pat. No. 5,756,466, U.S. Pat. No. 5,798,247, U.S. Pat. No. 5,798,442, U.S. Pat. No. 5,834,514, U.S. Pat. No. 5,843,904, U.S. Pat. No. 5,843,905, U.S. Pat. No. 5,847,135, U.S. Pat. No. 5,866,545, U.S. Pat. No. 5,843,904, U.S. Pat. No. 5,843,905, U.S. Pat. No. 5,847,135, U.S. Pat. No. 5,866,545, U.S. Pat. No. 5,869,519, U.S. Pat. No. 5,874,424, U.S. Pat. No. 5,932,549, Mjalli et al., *Bioorg. Med. Chem. Lett.* 3:2689–2693 (1993), Mjalli et al., *Bioorg. Med. Chem. Lett.* 4:1965–1968 (1994), Mjalli et al., *Bioorg. Med. Chem. Lett.* 5:1405–1408 (1995), Mjalli et al., *Bioorg. Med. Chem. Lett.* 5:1409–1414 (1995), Thornberry et al., *Biochem.* 33:3934–3940 (1994), Dolle et al., *J. Med. Chem.* 37: 563–564 (1994), Dolle et al., *J. Med. Chem.* 37: 3863–3866 (1994), Dolle et al., *J. Med. Chem.* 38: 220–222 (1995), Graybill et al., *Bioorg. Med. Chem. Lett.* 7:41–46 (1997), Semple et al., *Bioorg. Med. Chem. Lett.* 8:959–964 (1998), and Okamoto et al., *Chem. Pharm. Bull.* 47:11–21 (1999).

With regard to the caspase inhibitors described herein, useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Optional substituents include one or more alkyl; halo; haloalkyl; cycloalkyl; aryl optionally substituted with one or more lower alkyl, halo, haloalkyl or heteroaryl groups; aryloxy optionally substituted with one or more lower alkyl, halo, haloalkyl or heteroaryl groups; aralkyl; heteroaryl optionally substitued with one or more lower alkyl, haloalkyl and aryl groups; heteroaryloxy optionally substitued with one or more lower alkyl, haloalkyl and aryl groups; alkoxy; alkylthio; arylthio; amino; acyloxy; arylacyloxy optionally substituted with one or more lower alkyl, halo alkyl and aryl groups; diphenylphosphinyloxy optionally substituted with one or more lower alkyl, halo or haloalkyl groups; heterocyclo optionally substitued with one or more lower alkyl, haloalkyl and aryl groups; heterocycloalkyloxy optionally substitued with one or more lower alkyl, haloalkyl and aryl groups; partially unsaturated heterocycloalkyl optionally substituted with one or more lower alkyl, haloalkyl and aryl groups; or partially unsaturated heterocycloalkyloxy optionally substitued with one or more lower alkyl, haloalkyl and aryl groups.

Useful aryl groups are $C_{6-14}$ aryl, especially $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above. Also included are the sulfoxides and sulfones of such alkylthio groups.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g. 2,6-dichlorobenzoyloxy, 2,6-difluorobenzoyloxy and 2,6-di-(trifluoromethyl)-benzoyloxy groups.

Useful amino groups include —$NH_2$, —$NHR_{11}$, and —$NR_{11}R_{12}$, wherein $R_{11}$ and $R_{12}$ are $C_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Preferred N-terminal protecting groups include t-butyloxycarbonyl, acetyl and benzyloxycarbonyl.

Amino acids include any of the naturally occurring amino acids such as the L-forms of tyrosine, glycine, phenylalanine, methionine, alanine, serine, isoleucine, leucine, threonine, valine, proline, lysine, histidine, glutamine, glutamic acid, tryptophan, arginine, aspartic acid, asparagine and cysteine. Examples of non-natural amino acids include, without limitation, the enantiomeric and racemic forms of 2-methylvaline, 2-methylalanine, (2-i-propyl)-β-alanine, phenylglycine, 4-methylphenylglycine, 4-isopropylphenylglycine, 3-bromophenylglycine, 4-bromophenylglycine, 4-chlorophenylglycine, 4-methoxyphenylglycine, 4-ethoxyphenylglycine, 4-hydroxyphenylglycine, 3-hydroxyphenylglycine, 3,4-dihydroxyphenylglycine, 3,5-dihydroxyphenylglycine, 2,5-dihydrophenylglycine, 2-fluorophenylglycine, 3-fluorophenylglycine, 4-fluorophenylglycine, 2,3-difluorophenylglycine, 2,4-difluorophenylglycine, 2,5-difluorophenylglycine, 2,6-difluorophenylglycine, 3,4-difluorophenylglycine, 3,5-difluorophenylglycine, 2-(trifluoromethyl)phenylglycine, 3-(trifluoromethyl) phenylglycine, 4-(trifluoromethyl)phenylglycine, 2-(2-thienyl)glycine, 2-(3-thienyl)glycine, 2-(2-furyl)glycine, 3-pyridylglycine, 4-fluorophenylalanine, 4-chlorophenylalanine, 2-bromophenylalanine, 3-bromophenylalanine, 4-bromophenylalanine, 2-naphthylalanine, 3-(2-quinoyl) alanine, 3-(9-anthracenyl)alanine, 2-amino-3-phenylbutanoic acid, 3-chlorophenylalanine, 3-(2-thienyl) alanine, 3-(3-thienyl)alanine, 3-phenylserine, 3-(2-pyridyl) serine, 3-(3-pyridyl)serine, 3-(4-pyridyl)serine, 3-(2-thienyl)serine, 3-(2-furyl)serine, 3-(2-thiazolyl)alanine, 3-(4-thiazolyl)alanine, 3-(1,2,4-triazol-1-yl)-alanine, 3-(1,2,4-triazol-3-yl)-alanine, hexafluorovaline, 4,4,4-trifluorovaline, 3-fluorovaline, 5,5,5-trifluoroleucine, 2-amnino4,4,4-trifluorobutyric acid, 3-chloroalanine, 3-fluoroalanine, 2-amino-3-flurobutyric acid, 3-fluoronorleucine, 4,4,4-trifluorothreonine, L-allylglycine, tert-Leucine, propargylglycine, vinylglycine, S-methylcysteine, cyclopentylglycine, cyclohexylglycine, 3-hydroxynorvaline, 4-azaleucine, 3-hydroxyleucine, 2-amino-3-hydroxy-3-methylbutanoic acid, 4-thiaisoleucine, acivicin, ibotenic acid, quisqalic acid, 2-indanylglycine, 2-aminoisobutyric acid, 2-cyclobutyl-2-phenylglycine, 2-isopropyl-2-phenylglycine, 2-methylvaline, 2,2-diphenylglycine, 1-amino-I-cyclopropanecarboxylic acid, 1-amino-1-cyclopentanecarboxylic acid, 1-amino-1-cyclohexanecarboxylic acid, 3-amino-4,4,4-trifluorobutyric acid, 3-phenylisoserine, 3-amino-2-hydroxy-5-methylhexanoic acid, 3-amino-2-hydroxy4-phenylbutyric acid, 3-amino-3-(4-bromophenyl)propionic acid, 3-amino-3-(4-chlorophenyl)propionic acid, 3-amino-3-(4-methoxyphenyl)propionic acid, 3-amino-3-(4-fluorophenyl)propionic acid, 3-amino-3-(2-fluorophenyl)propionic acid, 3-amino-3-(4-nitrophenyl)propionic acid, and 3-amino-3-(1-naphthyl)propionic acid.

Certain of the compounds may exist as stereoisomers including optical isomers. The invention includes the use of all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy and Tris(hydroxymethyl) aminomethane (TRIS, tromethane).

Examples of prodrugs that may be used include compounds having substituted alkyl group such as $CH_2OCH_3$ and $CH_2COCH_3$ (AM ester).

The caspase inhibitors may be prepared according to methods well known in the art and by those methods in the publications, patent applications and patents cited herein.

The caspase inhibitors may be administered as part of a pharmaceutical composition comprising a pharmaceutically acceptable carrier, wherein the caspase inhibitors are present in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated. Preferably, about 0.01 to about 10 mg/kg is orally administered. For intramuscular injection, the dose is generally about one-half of the oral dose, e.g. about 0.0025 to about 25 mg/kg, and most preferably, from about 0.01 to about 5 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier. In a preferred embodiment, the compound is present at a concentration of about 0.07–1.0 mg/ml, more preferably, about 0.1 to 0.5 mg/ml, most preferably, about 0.4 mg/ml.

For veterinary uses, higher levels may be administered as necessary.

Suitable pharmaceutically acceptable carriers comprise excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as enemas and suppositories, as well as suitable solutions for administration by injection, topically or orally, contain from about 0.01 to 99 percent, preferably from about 0.25 to 75 percent of active compound(s), together with the excipient.

Also included within the scope of the present invention are the non-toxic pharmaceutically acceptable salts of the caspase inhibitors. Acid addition salts are formed by mixing a solution of the particular caspase inhibitor with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular caspase inhibitor with a solution of a pharmaceutically acceptable non-toxic base such as sodium hydroxide, potassium hydroxide, choline hydroxide, sodium carbonate Tris and the like.

The caspase inhibitors may be administered to any animal which may experience the beneficial effects of the invention. Foremost among such animals are mammals, e.g., humans, although the invention is not intended to be so limited.

The caspase inhibitors and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired. In general, the caspase inhibitors are administered locally to the tissues that are to be protected from apoptosis and separately from the chemotherapeutic agent. For example, cisplatin may be administered by i.v. injection to treat a cancer such as brain, lung, breast, liver, kidney, pancreatic, ovarian, prostatic cancer, and the caspase inhibitor administered locally to treat, ameliorate, or prevent apototic cell death in the mouth or gastrointestinal tract, such as a mouth wash for the treatment of oral mucositis; and IV injectable aqueous solution for the treatment of bone marrow cell death; and an oral formulation suitable for coating the gastrointestinal surfaces or an emema or suppository formulation for the treatment of gastrointestinal mucositis including proctitis. The caspase inhibitors may also be applied through a bladder catheter for the treatment, amelioration or prevention of bladder mucositis. Alternatively or concurrently, the caspase inhibitors may be applied topically to the skin and/or scalp to treat, ameliorate or prevent apoptotic cell death of hair and skin cells. In a further embodiment, the chemotherapeutic agent or radiation may be applied locally to treat a localized cancer such as brain, lung, breast, liver, kidney, pancreatic, ovarian, prostatic cancer, and the caspase inhibitor administered systemically, e.g. by i.v. injection, to treat, ameliorate or prevent apoptotic cell death of the gastrointestinal tract cells, mouth epithelial cells, bone marrow cells, skin cells and hair cells. In the case of oral mucositis in brain cancer treatment, for example, a caspase inhibitor that does not penetrate the blood-brain barrier can be applied, for example, systemically by i.v. injection followed by irradiation of the brain tumor. This would protect the oral mucosa from the harmful effects of radiation but the caspase inhibitor would not protect the brain tumor from the therapeutic effects of radiation. Importantly, the caspase inhibitor can be applied prior to administration of the radiation, thus preventing the onset of the damaging effects of the radiation to the normal mucosa cells.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered.

Suitable lipophilic solvents or vehicles include fatty oils, for example, sesame oil, or synthetic fatty acid esters, for example, ethyl oleate or triglycerides or polyethylene glycol-400 (the compounds are soluble in PEG400). Aqueous injection suspensions may contain substances which increase the viscosity of the suspension include, for example, sodium carboxymethyl cellulose, sorbitol, and/or dextran. Optionally, the suspension may also contain stabilizers.

One or more additional substances which have beneficial effects on the non-cancer cells may also be incorporated in the compositions. Thus, the composition may also contain one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are 5-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the pharmaceutical compositions include any compounds known to have a beneficial effect on skin. Such compounds include retinoids such as Vitamin A, in an amount of about 0.003–0.3% by weight and chromanols such as Vitamin E or a derivative thereof in an amount of about 0.1–10% by weight, both based on the weight of the composition. Additionally, anti-inflammatory agents and keratoplastic agents may be incorporated in the pharmaceutical compositions. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent that may be included in a topical composition for the skin is coal tar in an amount of about 0.1–20% or anthralin in an amount of about 0.05–2% by weight, both based on the weight of the composition.

The topical compositions may be formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the caspase inhibitor, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the caspase inhibitor in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the caspase inhibitor, in a suitable high molecular weight alcohol such as propylene glycol or polyethylene glycol.

In addition, these compositions may include other medicinal agents, growth factors, wound sealants, carriers, etc., that are known or apparent to those skilled in the art.

In a preferred embodiment, the caspase inhibitor is formulated as part of a mouthwash for the treatment, amelioration or prevention of oral mucositis. Such mouthwashes are aqueous solutions of the caspase inhibitor which may also contain alcohol, glycerin, synthetic sweeteners and surface-active, flavoring and coloring agents. They may also contain anti-infective agents such as hexetidine and cetylpyridinium chloride. The mouthwashes may also contain topical anesthetics (e.g. benzocaine, cocaine, dyclonine hydrochloride, lidocaine, proparacaine hydrochloride or teracaine hydrochloride), for example, for relieving pain of radiation or chemotherapy-induced sores. The mouth washes may have either acidic or basic pH. See Remington's Pharmaceutical Sciences, A. R. Gennaro (ed.), Mack Publishing Company, pp. 1045, 1046, 1526 and 1965 (1990).

In another preferred embodiment, the caspase inhibitor is formulated as an oral formulation which is capable of coating the gastrointestinal surfaces for the treatment, amelioration or prevention of gastrointestinal mucositis. Examples of gastrointestinal mucositis include esophageal mucositis, gastric mucositis, and intestinal mucositis. Such formulations may comprise gastric antacids such as aluminum carbonate, aluminum hydroxide gel, bismuth subnitrate, bismuth subsalicylate, calcium carbonate, dihydroxyaluminum sodium carbonate, magaldrate, magnesium carbonate, magnesium hydroxide, magnesium oxide, sodium bicarbonate, milk of bismuth, dihydroxyaluminum aminoacetate, magnesium phosphate, magnesium trisilicate and mixtures thereof. Other additives include without limitation $H_2$-receptor antagonists, digestants, anti-emetics, adsorbants, and miscellaneous agents. See Remington's Pharmaceutical Sciences, A. R. Gennaro (ed.), Mack Publishing Company, pp. 774–778 (1990).

Chemotherapy agents such as cisplatin and radiation therapy often induce early and late onset emesis in the patient. Thus, in one embodiment an antiemetic is coadministered together with the caspase inhibitor to avoid emesis and retain contact of the caspase inhibitor with the gastrointestinal tract. Examples of such antiemetics include without limitation compounds that block the dopaminergic emetic receptors such as metoclopramide and trimethobenzamide, and cannabinoids. Metoclopramide may be administered orally prior to and/or during chemotherapy/radiation therapy/caspase inhibitor therapy to prevent the early emesis response and then later by intranasal administration according to U.S. Pat. Nos. 5,760,086 and 4,536,386 to prevent delayed onset emesis. During the period after chemotherapy/radiation therapy, both the caspase inhibitor and the antiemetic may be coadministered to treat, ameliorate or prevent gastrointestinal mucositis.

In a further embodiment, the caspase inhibitor may be formulated as an IV injectable solution for the treatment, amelioration or prevention of bone marrow cell death.

The compositions may be administered to a warm-blooded animal, such as human, already suffering from chemotherapy or radiation therapy-induced non-cancer cell death, or, more preferably, before or during therapy with chemotherapy or radiation.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Caspase Inhibitor Z-VD-fmk Inhibits Apoptosis Induced by Chemotherapeutic Agents or UV Irradiation in Jurkat T Cells Jurkat T leukemia cells were grown in RPMI 1640 media (Life Technologies, Inc.)+10% FCS (Sigma Chemical Company) in a 5% $CO_2$ -95% humidity incubator at 37° C., and maintained at a cell density between 4 and $8\times10^5$ cells/ml. $1\times10^6$ cells were treated with Doxorubicin (1 $\mu$M) or Paclitaxel (20 $\mu$M) or UV irradiation (40 $J/m^2$) with or without the caspase inhibitor Z-VD-fmk (10 $\mu$M) and incubated at 37° C. for 18 h. As a control, cells were also incubated with DMSO. At 18 h cells were observed under phase contrast microscopy to visualize any morphological changes induced by the apoptotic stimuli. Cells were assessed for viability by a propidium iodide uptake assay. Briefly, 20 $\mu$l of propidium solution containing 100 $\mu$g/ml of propidium iodide was added to 200 $\mu$l of cells and transferred to 12×75mm polystyrene tubes and analyzed on a flow cytometer. All flow cytometry analyses were performed on FACScalibur (Becton Dickinson) using CellQuest analysis software. FIGS. 1A–D shows that Z-VD-fmk blocks doxorubicin induced cell death in Jurkat cells. FIGS. 2A–D shows that Z-VD-fmk blocks paclitaxel induced cell death in Jurkat cells. FIGS. 3A–D shows that Z-VD-fmk blocks UV irradiation induced cell death in Jurkat cells.

Figure 1B:
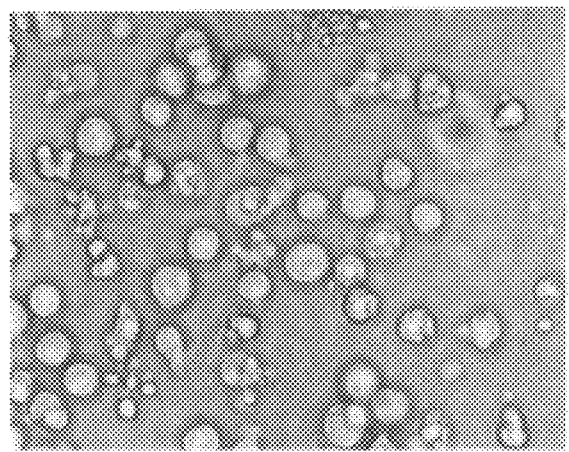
Figure 1C:
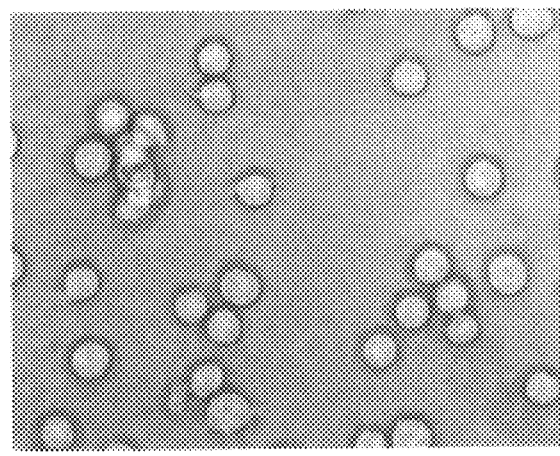
Figure 1D:
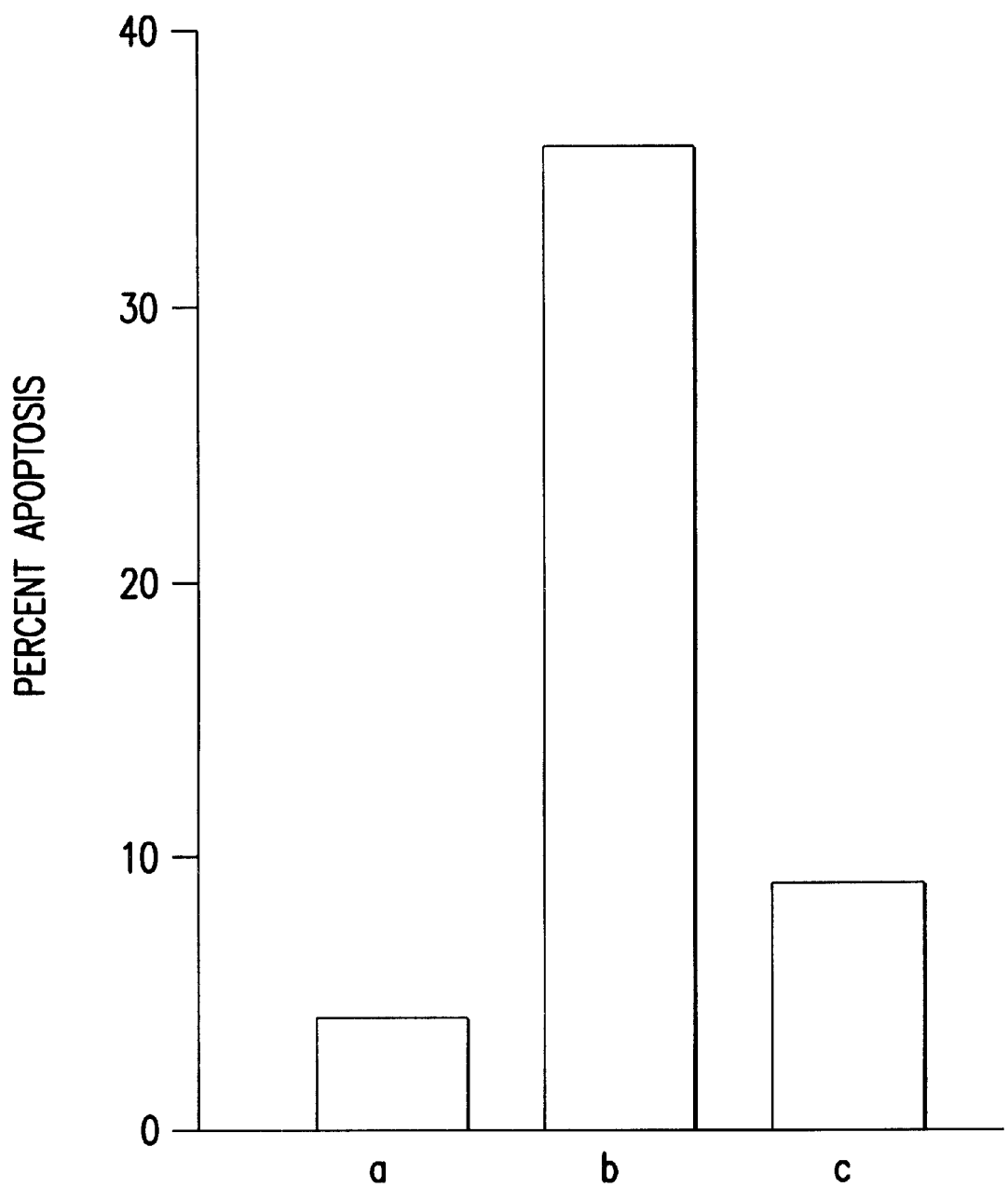
FIG. 1D depicts a bar graph showing percentage of cell apoptosis as measured by a propidium iodide uptake assay.

FIGS. 1A–C depict photographs of Jurkat cells: FIG. 1A, DMSO treated control cells; FIG. 1B, cells treated with doxorubicin (1 $\mu$M); FIG. 1C, cells treated with doxorubicin (1 $\mu$M) and Z-VD-fmk (10 $\mu$M). FIG. 1D depicts a bar graph showing percentage of cell apoptosis as measured by a propidium iodide uptake assay: a, DMSO treated control cells; b, cells treated with doxorubicin; c, cells treated with doxorubicin and Z-VD-fmk.

Figure 2A:
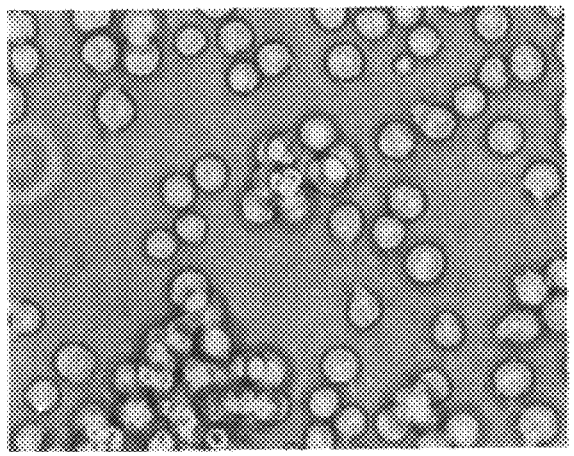
FIGS. 2A–C depict photographs of Jurkat cells.
Figure 2B:
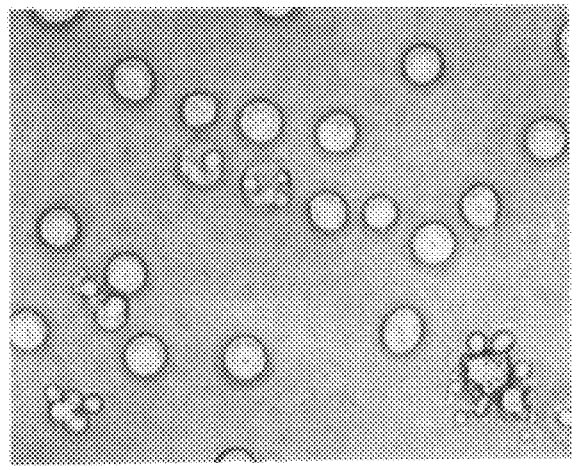
Figure 2C:
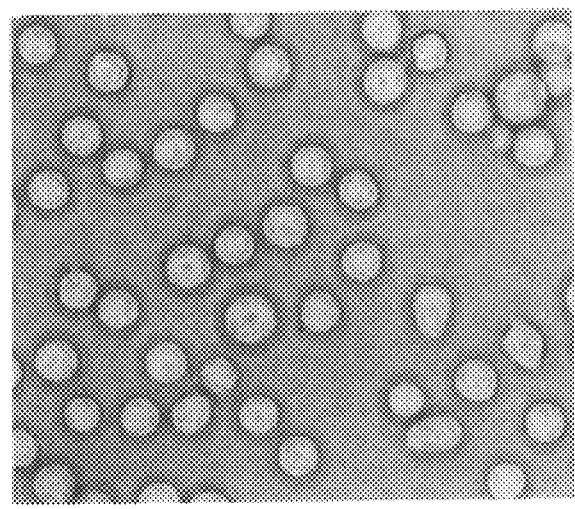
Figure 2D:
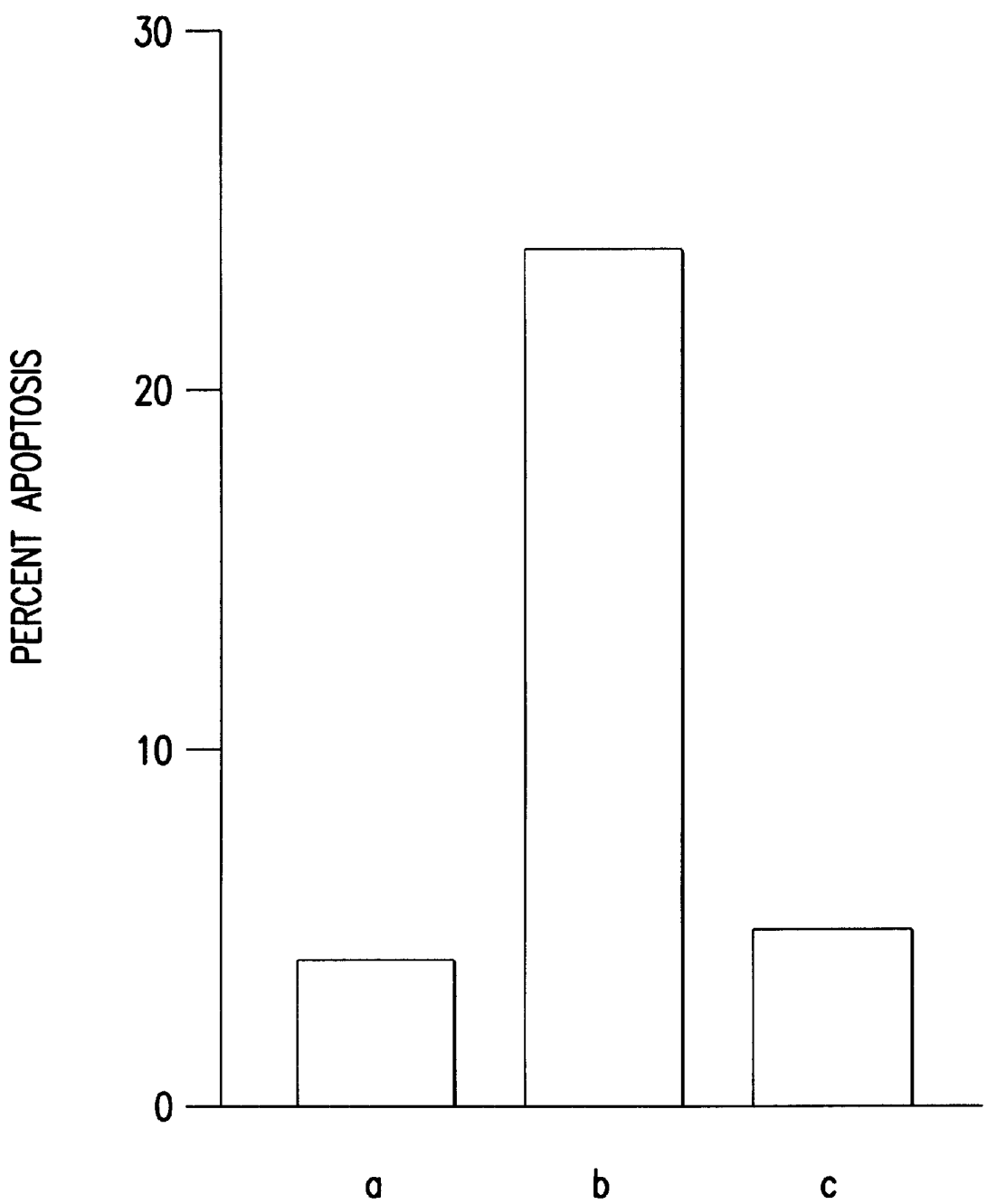
FIG. 2D depicts a bar graph showing percentage of cell apoptosis as measured by a propidium iodide uptake assay.

FIGS. 2A–C depict photographs of Jurkat cells: FIG. 2A, DMSO treated control cells; FIG. 2B, cells treated with paclitaxel (20 $\mu$M); FIG. 2C, cells treated with paclitaxel (20 $\mu$M) and Z-VD-fink (10 $\mu$M). FIG. 2D depicts a bar graph showing percentage of cell apoptosis as measured by a propidium iodide uptake assay: a, DMSO treated control cells; b, cells treated with paclitaxel; c, cells treated with paclitaxel and Z-VD-fink.

Figure 3A:
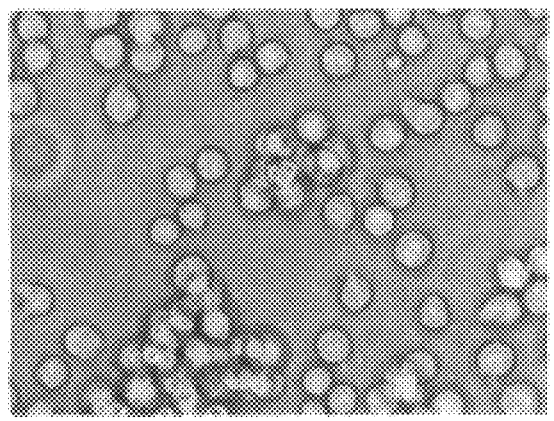
FIGS. 3A–C depict photographs of Jurkat cells.
Figure 3B:
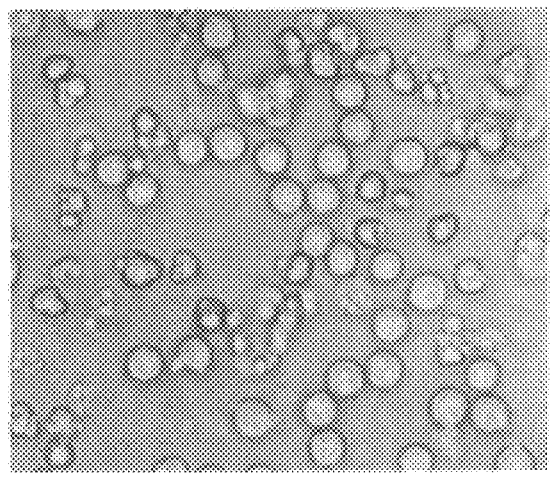
Figure 3C:
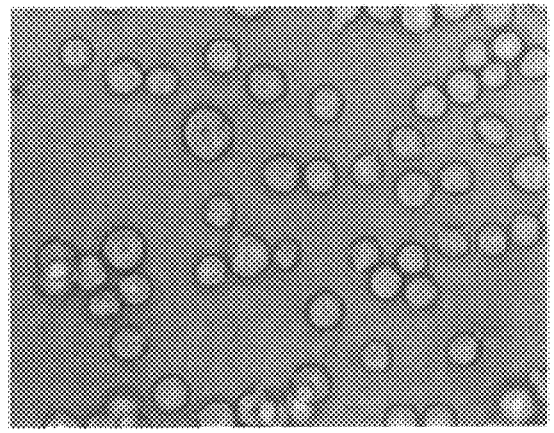
Figure 3D:
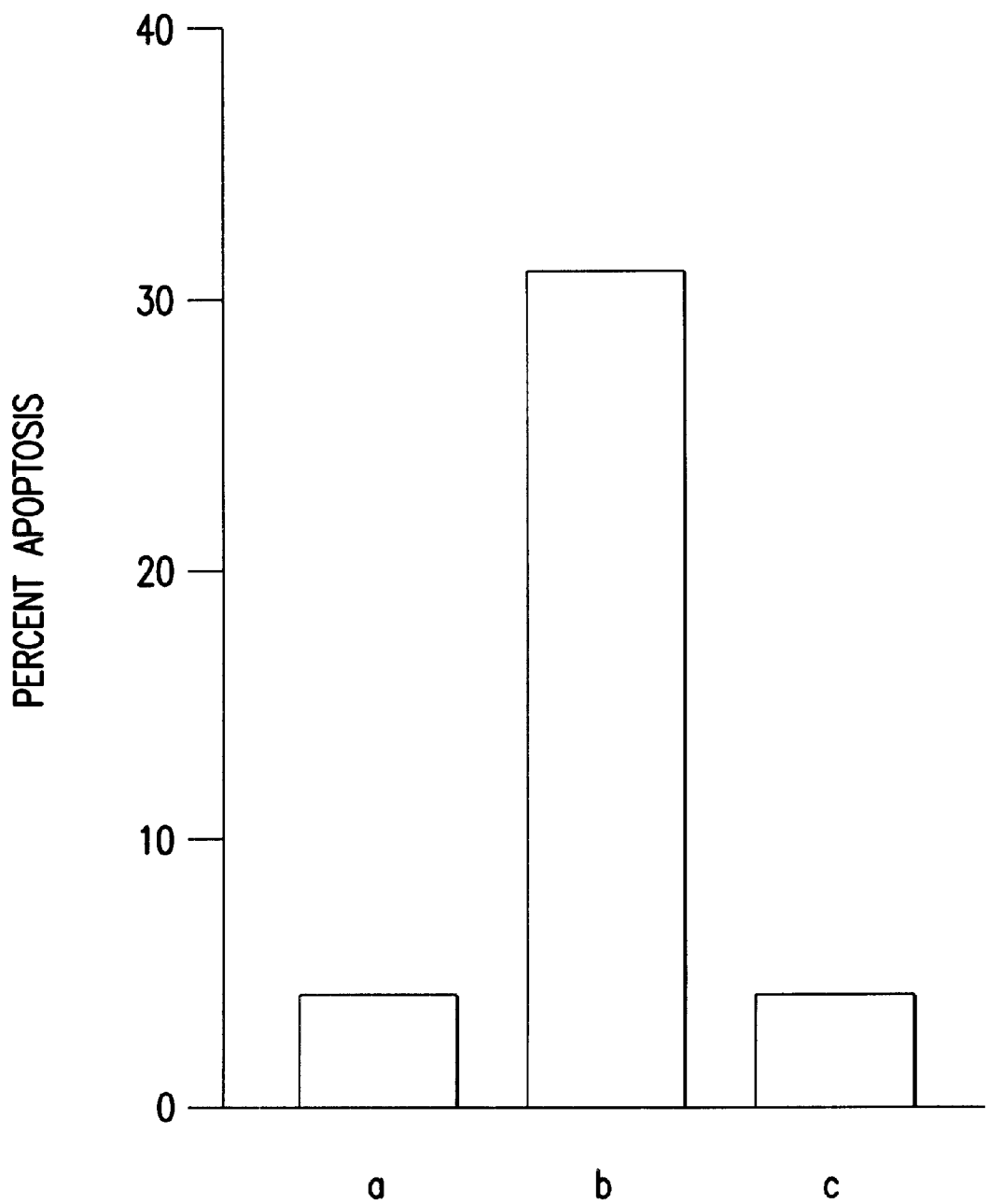
FIG. 3D depicts a bar graph showing percentage of cell apoptosis as measured by a propidium iodide uptake assay.

FIGS. 3A–C depict photographs of Jurkat cells: FIG. 3A, DMSO treated control cells; FIG. 3B, cells treated with UV irradiation (40 $J/m^2$); FIG. 3C, cells treated with UV irradiation (40 J/m2) and Z-VD-fmk (10 $\mu$M). FIG. 3D depicts a bar graph showing percentage of cell apoptosis as measured by a propidium iodide uptake assay: a, DMSO treated control cells; b, cells treated with UV irradiation; c, cells treated with UV irradiation and Z-VD-fmk.

EXAMPLE 2

Caspase Inhibitor (3R,S)-5-Fluoro-3-[(2S)-3-methyl-1-oxo-2-(phenylcarbamoyloxy)butyl]amino-4-oxo-pentanoic Acid Is Effective in Preventing the Development of Radiation-Induced Oral Mucositis in Hamsters Background Oral ulcerative mucositis is a common, painful, dose-limiting toxicity of drug and radiation therapy for cancer. The disorder is characterized by breakdown of the oral mucosa, which results in the formation of ulcerative lesions. In granulocytopenic patients, the ulcerations that accompany mucositis are frequent portals of entry for indigenous oral bacteria often leading to sepsis or bacteremia. Mucositis occurs to some degree in more than one third of all patients receiving anti-neoplastic drug therapy. The frequency and severity are significantly greater among patients who are treated with induction therapy for leukemia or with many of the conditioning regimens for bone marrow transplant. Among these individuals, moderate to severe mucositis (ulceration) is not unusual in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached.

Clinically mucositis progresses through four stages:

An initial stage which is characterized by inflammatory changes of erythema and edema. Localized islands of hyperkeratosis may also been seen. This stage is symptomatically mild and may be successfully palliated by topical anesthetics.

Subsequently the mucosa breaks down and becomes eroded and atrophic with increasingly significant inflammatory changes. This stage is increasingly painful and may require systemic analgesic therapy in the form of NSAIDs or oral narcotics for adequate palliation.

The third stage of mucositis is the most symptomatic. Full thickness ulcers of the mucosa cause severe discomfort necessitating parenteral narcotic therapy. In addition, in the myelosuppressive patient, these ulcerations provide a systemic portal of entry for the oral microflora often leading to bacteremia and sepsis. Antimicrobial intervention is required.

Finally, spontaneous healing occurs about 2–3 weeks after cessation of anti-neoplastic therapy.

Standard therapy for mucositis is predominantly palliative, including application of topical analgesics such as lidocaine and/or systemic administration of narcotics and antibiotics. Currently, there is no approved treatment for mucositis.

The complexity of mucositis as a biological process has only been recently appreciated. The condition appears to represent a sequential interaction of oral mucosal cells and tissues including connective tissue, endothelium, epithelium and inflammatory cells, pro-inflammatory cytokines and local environmental factors such as bacteria and saliva. Damage to epithelial and connective tissue induces release of inflammatory cytokines leading to mucosal damage. Additionally, both direct and indirect effects to epithelial cells result in either apoptotic or necrotic changes in the basal layer; differentiation into new epithelial cells is halted. The arrest of epithelial cell renewal leads to atrophy followed by ulceration.

A hamster model of chemotherapy-induced mucositis and, more recently, a model of radiation-induced mucositis has been developed (Sonis S. et al. *Oral Surg. Oral. Med. Oral Pathol.* 69:437–443 (1990) and Sonis S. et al. *Cancer*, 85:2103–13 (1999)). In the latter model, specific doses of acute radiation are targeted to the designated mucosa, with protection of other areas by a customized lead shield. The reproducibility of the model has been validated, with the consistent appearance of ulcerative mucositis between days 15 and 18 following radiation. Using this model, the efficacies of various topical agents have been tested for their abilities to modify the course of radiation-induced mucositis.

Objective

The objective of this study was to assess the effect of the topical and IP administration of (3R,S)-5-fluoro-3-[(2S)-3-methyl-1-oxo-2-(phenylcarbam-oyloxy)butyl]amino-4-oxo-pentanoic acid (a caspase inhibitor described in U.S. Application Ser. Nos. 60/151,077 and 60/158,373), in attenuating the development and progress of oral mucositis induced by acute irradiation in hamsters. Mucositis scores in hamsters receiving different doses of the compound were compared to those in hamsters receiving vehicle control, in order to detect statistically significant differences in the onset, duration or severity of the disorder.

Study Design

Thirty-two (32) hamsters were randomly divided into four treatment groups with eight (8) animals per group. Each group was assigned a different treatment as follows:

Group 1: Vehicle control—topical vehicle control, tid (3 times daily), day −2 to day 16.

Group 2: Test compound at 20 mg/kg, IP once per day, day −2 to day 16.

Group 3: Test compound at 0.36 mg/ml (0.2 ml), topical, tid, day −2 to day 16.

Group 4: Test compound at 0.072 mg/ml (0.2 ml), topical, tid, day −2 to day 16.

A flow chart for the events in this study is summarized below:

i) Every day for the period of the study (day −2 to day 28), each animal was weighed and its survival recorded (to accommodate the schedules of the study site weights were taken every other day starting on day 17 and continuing to day 28).

ii) Each animal in group 2 was injected IP once on day −2 and once on 20 day −1.

iii) Each animal in groups 1, 3 & 4 were dosed three times on day −2 and day −1.

iv) Each animal was irradiated on day 0.

v) Animals in groups 1, 3 & 4 were dosed 1 h prior to irradiation and twice after irradiation on day 0.

vi) Animals in groups 1, 3 & 4 were dosed 3 times daily with a topical dose from day −2 to day 16.

vii) Animals in group 2 received a single daily IP injection from day −2 to day 16.

viii) Starting on day 6 and continuing every second day thereafter (days 8, 10, 12, 14, 16, 18, 20, 22, 24, 26 & 28), each animal was photographed and evaluated for mucositis scoring.

Material And Methods

Study Location(s)

Irradiation of the animals was carried out at the Dana Farber Cancer Institute. The study was conducted at The University of Massachusetts Medical Center, Worcester, Mass.

Animals

Male Golden Syrian hamsters (Charles River Laboratories or Harlan Sprague Dawley), aged 5 to 6 weeks, with body weights of approximately 90 g at project commencement, were used. Animals were individually numbered using an ear punch and housed in small groups of 2 animals per cage. Animals were acclimatized for at least one week prior to project commencement. During this period, the animals were observed daily in order to reject animals that present poor condition.

Mucositis Induction Mucositis was induced using an acute radiation protocol. A single dose of radiation (35 Gy/dose) was administered to all animals on Day 0. Radiation was generated with a 250 kilovolt potential (15-mA) source at a focal distance of 50 cm, hardened with a 0.35 mm Cu filtration system. Irradiation targeted the left buccal pouch mucosa at a rate of 121.5 cGy/minute. Prior to irradiation, animals were anesthetized with an intraperitoneal injection of sodium pentobarbital (80 mg/kg). The left buccal pouch was everted, fixed and isolated using a lead shield.

Dosing and Drug Application

Topical dosing of animals was done three times per day. For topical treatments, a needleless tuberculin syringe, containing 0.2 ml of the test compound in 0.05M Tris (pH 8.0), was inserted into the left cheek pouch and the drug deposited into the pouch. Intraperitoneal injections of the compound were done once a day at a dose of 20 mg/kg and a drug concentration of 3–6 mg/ml in 0.05M Tris (pH 8.0). Dosing began on day −2 for all groups. In all groups treatment continued until day 16.

Mucositis Evaluation The mucositis score, weight change and survival were measured as outcomes in this study. For the evaluation of mucositis, the animals were anesthetized with inhalation anesthetics, and the left pouch everted. Mucositis was scored visually by comparison to a validated photographic scale, ranging from 0 for normal, to 5 for severe ulceration (clinical scoring). In descriptive terms, this scale is defined as follows:

| Score: | Description: |
| --- | --- |
| 0 | Pouch completely healthy. No erythema or vasodilation |
| 1 | Light to severe erythema and vasodilation. No erosion of mucosa |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative size of ulcers should equal about ½ of the pouch. Loss of pliability. Severe erythema and vasodilation. |
| 5 | Virtually all of pouch is ulcerated. Loss of pliability (pouch can only partially be extracted from mouth) |

A score of 1–2 is considered to represent a mild stage of the disease, whereas a score of 3–5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above described scale (blinded scoring).

Assessment of Results

Statistical differences between treatment groups was determined using Student's t-test, Mann-Whitney rank sum and chi-square analysis with a critical value of 0.05. The N for each group was either 7 (Groups 2 & 3) or 8 (groups 1 & 4), an adequate number for the statistics proposed here. The differences in group size were a consequence of anesthesia deaths described below.

Results And Discussion

Study Characteristics There were two deaths during the course of this study. The first death (animal #23 in the 0.36 mg/ml topical treatment group) occurred on day 8, and the second death (animal #9 in the 20 mg/kg IP group) occurred on day 15. Both deaths were due to anesthesia overdose. The lack of mortality due to the treatment indicates that there is no systemic toxicity associated with the test compounds at the doses used here.

In the vehicle control group, mucositis began on day 10 and reached a peak on day 16. The peak score for this group was 4.0 on day 16 and remained above 3.0 until day 22. The course of mucositis in this study is typical of that commonly observed using the radiation protocol.

Figure 4:
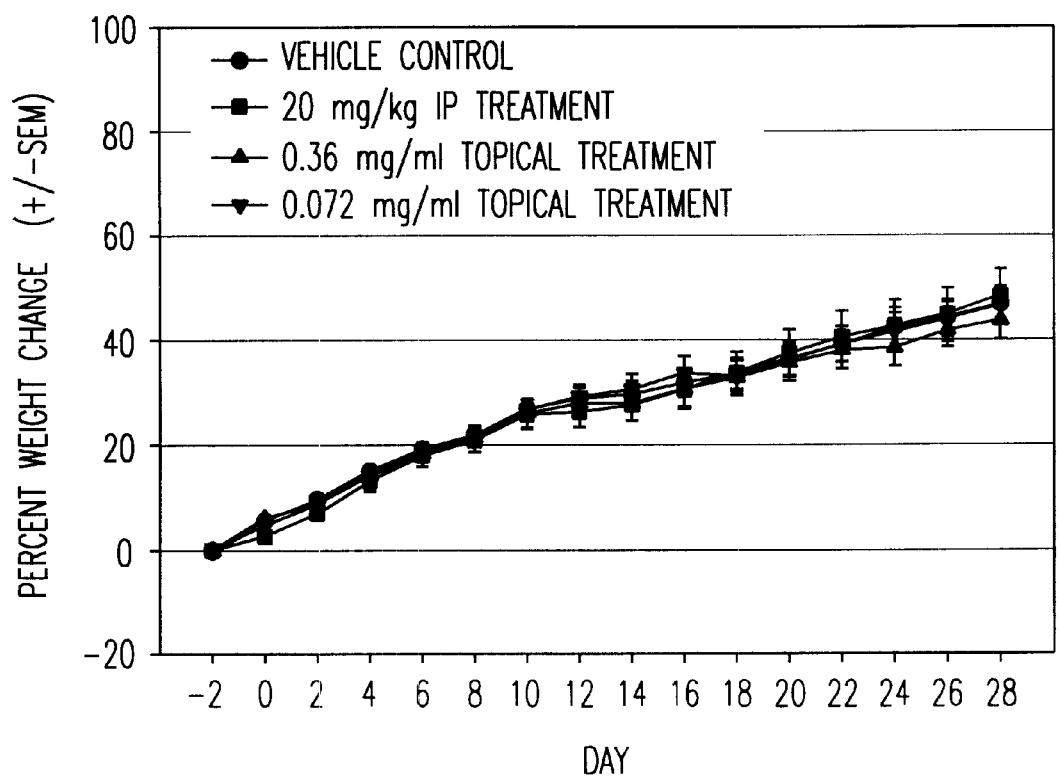
FIG. 4 depicts a plot showing the percent weight change of control and treated animals.

Weight The Vehicle Control Group: Examination of the daily change in animal weight (by percentage compared to the individual weights on day −2) indicates that the animals in the vehicle control group gained about 45% of the starting weight over the course of the study (FIG. 4). This robust weight gain is characteristic of untreated hamsters in the radiation protocol.

The Treatment Groups: All three groups that received treatment with the test compound gained weight in a nearly linear manner and finished the study having gained from 42 to 45% of their starting weights (FIG. 4). The weight gain by all treated animals in these groups is statistically equivalent to the vehicle control group.

Mucositis

Figure 5:
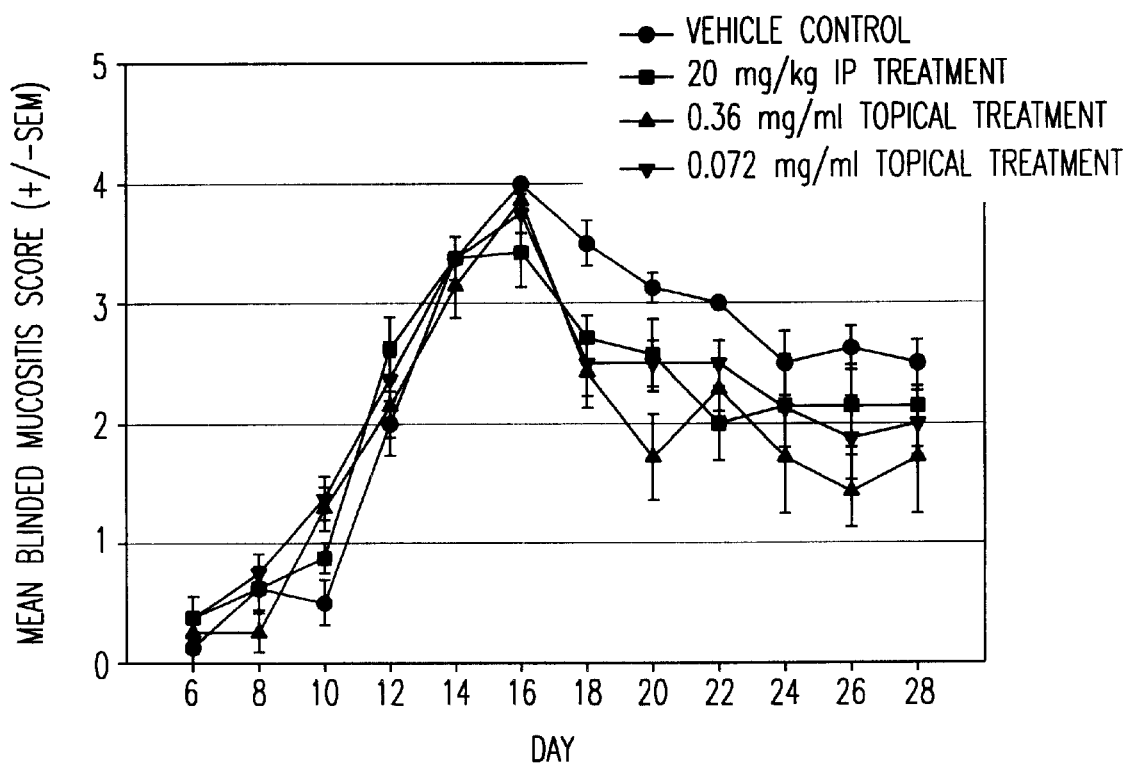
FIG. 5 depicts a plot showing the mean group mucositis scores of control and treated animals.
Figure 6:
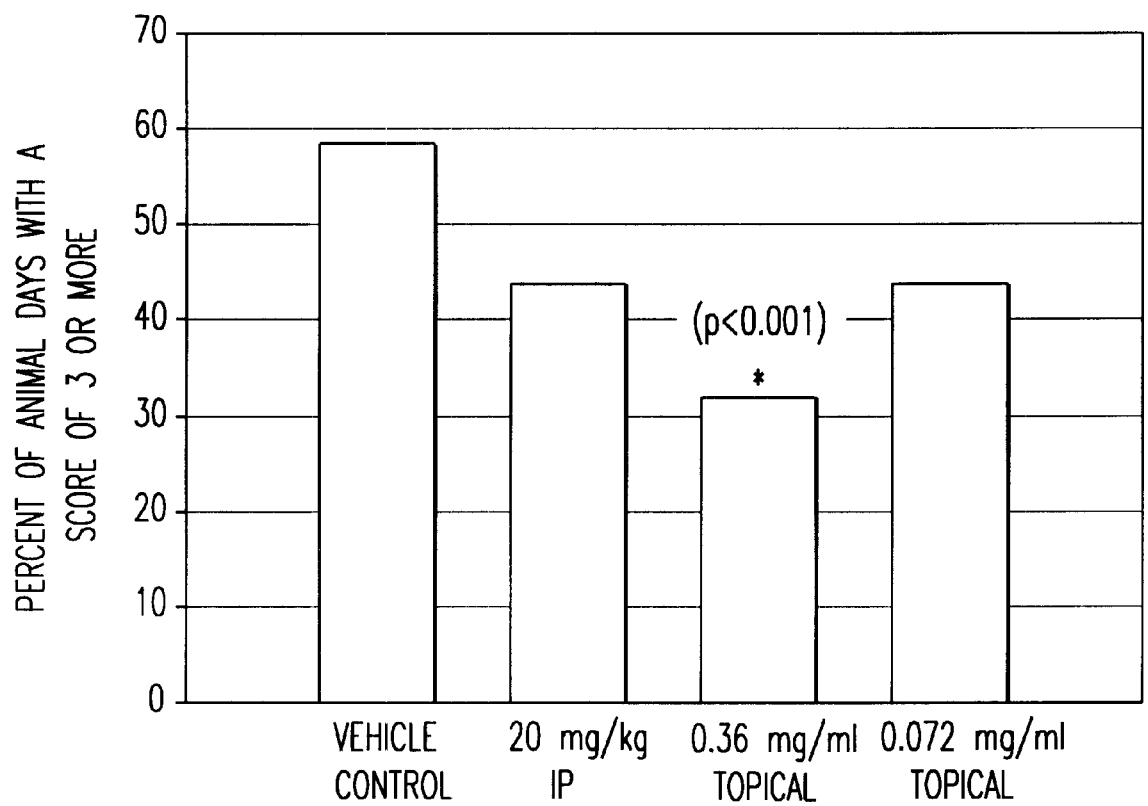
FIG. 6 depicts a bar graph showing percent of animal days with mucositis scores of 3 or greater for control and treated animals.

The Vehicle Control Group: Mean daily mucositis scores for the vehicle control group is shown in FIG. 5. The course of mucositis in the vehicle control group is typical for the acute radiation model. Mucositis appears on day 10 and peak mucositis occurs on day 16 as described above. The peak mucositis score is 4.0. Mucositis remains elevated until day 22 when the scores drop below 3.0. Because of the clinical significance of a score of three or more, the amount of time an animal has an ulceration was determined for the entire study (FIG. 6). In the vehicle control group animals had scores of 3 or more on 58.3% of the possible days.

Intraperitoneal Injection of 20 mg/kg (Group 2): The intraperitoneal injection of 20 mg/kg of test compound from day −2 to day 16 resulted in an apparent reduction of mucositis from day 16 to day 28 when compared to the vehicle control group (FIG. 5). Rank sum analysis of comparing the daily scores from the vehicle control group with the IP treated group indicated a significant reduction in mucositis severity on days 20 and 22.

The analysis of animal days with a score of 3 or more (FIG. 6) shows that this treatment reduces the extent of ulceration when compared to the vehicle control group. The group treated with 20 mg/kg of test compound from day −2 to day 16 spent 39 days with ulcerations as compared to the 56 days of ulceration spent by the vehicle control group. The 24.8% reduction in ulceration effected by extended IP treatment did not achieve statistical significance (p=0.068).

Topical Treatments of 0.36 mg/ml and 0.072 mg/ml (Groups 3 & 4): The topical treatment with either 0.36 mg/ml or 0.072 mg/ml of test compound from day −2 to day 16 both resulted in an apparent reduction of mucositis from day 16 to day 28 when compared to the vehicle control group (FIG. 5). Rank sum analysis of comparing the daily scores from the vehicle control group with the topical 0.36 mg/ml group indicated a significant reduction of mucositis on days 18, 20, 22 & 26. Rank sum analysis of comparing the daily scores from the vehicle control group with the topical 0.072 mg/ml group indicated a less significant reduction of mucositis. Significance was achieved only on day 18. The rank sum analysis suggests a dose response to the compound.

The analysis of animal days with a score of 3 or more (FIG. 6) shows that both topical treatments reduce the extent of ulceration when compared to the vehicle control group. The group treated with 0.36 mg/ml of test compound from day −2 to day 16 spent 27 days with ulcerations as compared to the 56 days of ulceration spent by the vehicle control group. The 51.8 % reduction in ulceration effected by topical treatment at 0.36 mg/ml is highly significant (p<0.001). The group treated with 0.072 mg/ml of test compound from day −2 to day 16 spent 42 days with ulcerations as compared to the 56 days of ulceration spent by the vehicle control group. The 25% reduction in ulceration effected by topical treatment at 0.072 mg/ml is not significant (p=0.061). Thus both the rank sum and chi square analyses indicate a dose response with the topical treatment with the 0.36 mg/ml dose showing significant efficacy by independent statistical methods.

Conclusion

Topical administration of the test compound at 0.36 mg/ml from day −2 to day 16 showed a statistically significant benefit in preventing the development of significant mucositis in this model. The compound used topically at a concentration of 0.072 mg/ml demonstrated a reduction of mucositis scores, but the data did not achieve statistical significance in this study. These results suggest a dose response for the topical treatment.

Intraperitoneal application of test compound at 20 mg/kg, while demonstrating a trend toward mucositis reduction, also failed to achieve significance when compared to the vehicle control group.

The effect of test compound on oral mucositis occurred after the achievement of peak mucositis on day 16. There was no apparent reduction in the onset of ulceration from day 0 to day 16.

The test compound appears to have no toxicity at the doses applied in this study as indicated both by the absence of animal deaths during the study (other than those due to anesthesia overdose) and by a weight gain pattern for all treated groups that was nearly identical with that of the control group.

FIG. 4. Percent weight change. Animals were weighed daily and group means and standard errors of the mean (SEM) calculated for each day. Over the course of this study, the animals in all four study groups gained weight in a nearly identical manner.

FIG. 5. Mean group mucositis scores were obtained for all four animal groups in this study. Error bars represent the standard error of the mean (SEM). Comparison of the vehicle control group with the groups receiving test compound either topically or through intraperitoneal injection (IP). None of the treatment groups, when compared to the vehicle control group, show a reduction in the onset and severity of mucositis from day 10 to day 16. In contrast, all three treatments demonstrate a reduction in mucositis severity during the recovery phase of the disease after day 16.

FIG. 6. Animal days with mucositis scores of 3 or greater. To examine the levels of clinically significant mucositis, as defined by presentation with open ulcers (a score of 3 or greater), the total number of days in which an animal exhibited an elevated score were summed and expressed as a percentage of the total number of days. Statistical significance of observed differences was calculated using chi-square analysis. Asterisks indicate significant differences between individual treatment groups and placebo animals. In comparison with the vehicle control group, all three treatment groups demonstrated a reduction in overall mucositis severity in this study. Only the treatment with 0.36 mg/ml of test compound showed statistical significance (p<0.001).

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating or ameliorating oral mucositis, gastrointestinal mucositis, bladder mucositis or proctitis, resulting from chemotherapy or radiation therapy of cancer in an animal, comprising administering to the animal in need thereof an effective amount of a caspase inhibitor such that said oral mucositis, gastrointestinal mucositis, bladder mucositis or proctitis is treated or ameliorated, wherein said caspase inhibitor comprises a C-terminal aspartate-fluoromethylketone group.

2. The method of claim 1, wherein said caspase inhibitor is administered topically or orally.

3. The method of claim 2, wherein said caspase inhibitor is formulated as a mouthwash for the treatment or amelioration of oral mucositis.

4. The method of claim 2, wherein said caspase inhibitor is formulated as a slow release buccal lozenge.

5. The method of claim 2, wherein said caspase inhibitor is formulated as a suppository.

6. The method of claim 2, wherein said caspase inhibitor is formulated as a gel.

7. The method of claim 1, wherein said caspase inhibitor is administered through a bladder catheter for the treatment or amelioration of bladder mucositis.

8. The method of claim 1, wherein said caspase inhibitor is formulated as an enema for the treatment or amelioration of proctitis.

9. The method of claim 2, wherein said caspase inhibitor is formulated as an oral formulation which Is capable of coating the gastrointestinal surfaces for the treatment or amelioration of gastrointestinal mucositis.

10. The method of claim 9, wherein said gastrointestinal mucositis is esophageal mucositis, gastric mucositis, or intestinal mucositis.

11. The method of claim 1, wherein said caspase inhibitor is administered as a pharmaceutical composition comprising a pharmaceutically acceptable carrier.

12. The method of claim 1, wherein said caspase inhibitor has the formula:

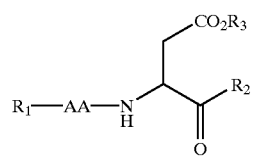

I or a pharmaceutically acceptable salt thereof;
wherein $R_1$ is an N-terminal protecting group;
AA is a residue of any natural or non-natural a-amino acid or β-amino acid;
$R_2$ is $CH_2F$; and
$R_3$ is alkyl or H.

13. The method of claim 12, wherein said caspase inhibitor is Boc-Ala-Asp-$CH_2F$, Boc-Val-Asp-$CH_2F$, Boc-Leu-Asp-$CH_2F$, Ac-Val-Asp-$CH_2F$, Ac-Ile-Asp-$CH_2F$, Ac-Met-Asp-$CH_2F$, Cbz-Val-Asp-$CH_2F$, Cbz-β-Ala-Asp-$CH_2F$, Cbz-Leu-Asp-$CH_2F$, Cbz-Ile-Asp-$CH_2F$, Boc-Ala-Asp(OMe)-$CH_2F$, Boc-Val-Asp(OMe)-$CH_2F$, Boc-Leu-Asp(OMe)-$CH_2F$, Ac-Val-Asp(OMe)-$CH_2F$, Ac-Ile-Asp(OMe)-

CH₂F, Ac-Met-Asp(OMe)-CH₂F, Cbz-Val-Asp(OMe)-CH₂F, Cbz-β-Ala-Asp(OMe)-CH₂F, Cbz-Leu-Asp(OMe)-CH₂F or Cbz-Ile-Asp(OMe)-CH₂F, wherein Boc is tert-butylcarbonyl, Ac is acetyl and Cbz is carbobenzyloxy.

14. The method of claim 1, wherein said caspase inhibitor has the formula II:

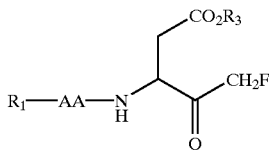

or a pharmaceutically acceptable salt thereof;
wherein $R_1$ is an N-terminal protecting group;
AA is a residue of a non-natural α-amino acid or β-amino acid; and
$R_2$ is an optionally substituted alkyl or H.

15. The method of claim 14, wherein said caspase inhibitor is Boc-Phg-Asp-fmk, Boc-(2-F-Phg)-Asp-fmk, Boc-(F₃-Val)-Asp-fmk, Boc-(3-F-Val)-Asp-fmk, Ac-Phg-Asp-fmk, Ac-(2-F-Phg)-Asp-fmk, Ac-(F₃-Val)-Asp-fmk, Ac-(3-F-Val)-Asp-fmk, Z-Phg-Asp-fmk, Z-(2-F-Phg)-Asp-fmk, Z-(F₃-Val)-Asp-fmk, Z-Chg-Asp-fmk, Z-(2-Fug)-Asp-fmk, Z-(4-F-Phg)-Asp-fmk, Z-(4-Cl-Phg)-Asp-fmk, Z-(3-Thg)-Asp-fmk, Z-(2-Fua)-Asp-fmk, Z-(2-Tha)-Asp-fmk, Z-(3-Fua)-Asp-fmk, Z-(3-Tha)-Asp-fmk, Z-(3-Cl-Ala)-Asp-fmk, Z-(3-F-Ala)-Asp-fmk, Z-(F₃-Ala)-Asp-fmk, Z-(3-F-3-Me-Ala)-Asp-fmk, Z-(3-Cl-3-F-Ala)-Asp-fmk, Z-(2-Me-Val)-Asp-fmk, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-(3-CF₃-Ala)-Asp-fmk, Z-(4-CF₃-Phg)-Asp-fmk, Z-(3-Me₂N-Ala)-Asp-fmk, Z-(2-Abu)-Asp-fmk, Z-Tle-Asp-fmk, Z-Cpg-Asp-fmk, Z-Cbg-Asp-fmk, Z-Thz-Asp-fmk, Z-(3-F-Val)-Asp-fmk, or Z-(2-Thg)-Asp-fmk, wherein Boc is tert-butylcarbonyl, Phg is phenylglycine, fmk is fluoromethylketone, Z is benzyloxycarbonyl, Chg is cyclohexlglycine, Fug is furylglycine, Thg is thienylglycine, Fua is furylalanine, Tha is thienylalanine, Nal is naphthylalanine, Cha is cyclohexlalanine, Abu is aminobutyric acid, Tle is tert-leucine, Cpg is cyclopentylglycine, Cbg is cyclobutylglycine and Thz is thioproline.

16. The method of claim 1, wherein said caspase inhibitor is administered after chemotherapy or radiation therapy of cancer in said animal.

17. The method of claim 1, wherein said caspase inhibitor is administered during chemotherapy or radiation therapy of cancer in said animal.

18. The method of claim 1, wherein said caspase inhibitor is administered prior to chemotherapy or radiation therapy of cancer in said animal.

19. The method of claim 14, wherein said optional substituents is selected from the group consisting of alkyl; halo; haloalkyl; cycloalkyl; aryl optionally substituted with one or more lower alkyl, halo, haloalkyl or heteroaryl groups; aryloxy optionally substituted with one or more lower alkyl, halo, haloalkyl or heteroaryl groups; aralkyl; heteroaryl optionally substituted with one or more lower alkyl, haloalkyl and aryl groups; heteroaryloxy optionally substituted with one or more lower alkyl, haloalkyl and aryl groups; alkoxy; alkylthio; arylthio; amino; acyloxy; arylacyloxy optionally substituted with one or more lower alkyl, halo alkyl and aryl groups; diphenylphosphinyloxy optionally substituted with one or more lower alkyl, halo, or haloalkyl groups; heterocycloalkyloxy optionally substituted with one or more lower alkyl, haloalkyl and aryl groups; partially unsaturated heterocycloalkyl optionally substituted with one or more lower alkyl, haloalkyl and aryl groups; and partially unsaturated heterocycloalkyloxy optionally substituted with one or more lower alkyl, haloalkyl and aryl groups.

* * * * *